(12) United States Patent
Grison et al.

(10) Patent No.: US 9,744,391 B2
(45) Date of Patent: Aug. 29, 2017

(54) USE OF METAL-ACCUMULATING PLANTS FOR IMPLEMENTING CHEMICAL REACTIONS

(71) Applicants: CENTRE NATIONAL DE LA RECHERCHE SCIENTIFIQUE, Paris (FR); UNIVERSITE MONTPELLIER 2 SCIENCES ET TECHNIQUES, Montpellier (FR)

(72) Inventors: Claude Grison, Castelnau-le-lez (FR); Jose Escarre, Montpellier (FR)

(73) Assignees: CENTRE NATIONAL DE LA RECHERCHE SCIENTIFIQUE, Paris (FR); UNIVERSITE MONTPELLIER 2 SCIENCES ET TECHNIQUES, Montpellier (FR)

( * ) Notice: Subject to any disclaimer, the term of this patent is extended or adjusted under 35 U.S.C. 154(b) by 18 days.

(21) Appl. No.: 14/831,987

(22) Filed: Aug. 21, 2015

(65) Prior Publication Data
US 2015/0360066 A1    Dec. 17, 2015

Related U.S. Application Data

(62) Division of application No. 13/512,187, filed as application No. PCT/FR2010/052451 on Nov. 18, 2010, now Pat. No. 9,149,796.

(30) Foreign Application Priority Data

Nov. 26, 2009    (WO) ................. PCT/FR2009/052312

(51) Int. Cl.
| | |
|---|---|
| C07C 321/00 | (2006.01) |
| A62D 3/35 | (2007.01) |
| B01J 23/06 | (2006.01) |
| B01J 23/72 | (2006.01) |
| B01J 23/755 | (2006.01) |
| C07C 29/62 | (2006.01) |
| C07C 2/86 | (2006.01) |
| C07C 17/16 | (2006.01) |
| C07C 41/30 | (2006.01) |
| C07C 45/00 | (2006.01) |
| C07C 67/02 | (2006.01) |
| C07C 67/347 | (2006.01) |
| C07C 209/32 | (2006.01) |
| C07D 239/22 | (2006.01) |
| C07F 1/08 | (2006.01) |
| A62D 101/04 | (2007.01) |

(52) U.S. Cl.
CPC ............... *A62D 3/35* (2013.01); *B01J 23/06* (2013.01); *B01J 23/72* (2013.01); *B01J 23/755* (2013.01); *C07C 2/861* (2013.01); *C07C 17/16* (2013.01); *C07C 29/62* (2013.01); *C07C 41/30* (2013.01); *C07C 45/00* (2013.01); *C07C 67/02* (2013.01); *C07C 67/347* (2013.01); *C07C 209/32* (2013.01); *C07D 239/22* (2013.01); *C07F 1/08* (2013.01); *A62D 2101/04* (2013.01); *C07C 2523/04* (2013.01); *C07C 2527/122* (2013.01); *C07C 2527/128* (2013.01); *C07C 2527/138* (2013.01)

(58) Field of Classification Search
CPC ................................ C07F 9/02; C07C 321/00
USPC ....................................................... 568/16, 18
See application file for complete search history.

(56) References Cited

U.S. PATENT DOCUMENTS

| | | | |
|---|---|---|---|
| 4,525,218 | A | 6/1985 | Chen et al. |
| 2005/0217174 | A1 | 10/2005 | Angle et al. |
| 2008/0008676 | A1 | 1/2008 | Janardanan Nair et al. |
| 2008/0134364 | A1 | 6/2008 | Chaney et al. |
| 2012/0316340 | A1 | 12/2012 | Grison et al. |

FOREIGN PATENT DOCUMENTS

| | | |
|---|---|---|
| CN | 101381351 | 3/2009 |
| EP | 1806177 | 7/2007 |
| EP | 2327476 | 6/2011 |
| GB | 1604768 | 12/1981 |
| JP | 8311358 | 11/1996 |
| JP | 2004167376 | 6/2004 |
| WO | 9429226 | 12/1994 |
| WO | 9734714 | 9/1997 |
| WO | 0028093 | 5/2000 |
| WO | 2005094418 | 10/2005 |
| WO | 2006009661 | 1/2006 |
| WO | 2006096472 | 9/2006 |
| WO | 2007083304 | 7/2007 |
| WO | 2011064462 | 6/2011 |
| WO | 2011064487 | 6/2011 |
| WO | 2013150197 | 10/2013 |
| WO | 2014016509 | 1/2014 |

OTHER PUBLICATIONS

Yang et al., "Heavy metal removal and crude bio-oil upgrade from Sedum alfredii Hance harvest using hydrothermal upgrading", Journal of Hazardous Materials, 2010, vol. 179, pp. 1037-1041.

(Continued)

*Primary Examiner* — Yong Chu
*Assistant Examiner* — Sonya Wright
(74) *Attorney, Agent, or Firm* — Young & Thompson

(57) ABSTRACT

A method of implementing organic synthesis reactions uses a composition containing a metal catalyst originating from a calcined plant. The plants can be from the Brassicaceae, Sapotaceae and Convolvulaceae family, and the metal catalyst contains metal in the M(II) form such as zinc, nickel, manganese, lead, cadmium, calcium, magnesium or copper. Examples of the organic synthesis reactions include halogenations, electrophilic reactions, cycloadditions, transesterification reactions and coupling reactions, among others.

22 Claims, 4 Drawing Sheets

(56) References Cited

OTHER PUBLICATIONS

Yang et al., "Heavy metal removal and crude bio-oil upgrading from Sedum plumbizincicola harvest using hydrothermal upgrading process", Bioresource Technology, 2010, vol. 101, pp. 7653-7657.
Hu et al., "Tolerance, accumulation and distribution of zinc and cadmium in hyperaccumulator Potentilla griffithii", Environmental and Experimental Botany, 2009, vol. 66, pp. 317-325.
Zhang et al., "A newly found cadmium accumulator—Malva sinensis Cavan", Journal of Hazardous Materials, 2010, vol. 173, pp. 705-709.
Vamerali et al., "Field crops for phytoremediation of metal-contaminated land", Environ. Chem. Lett., 2010, vol. 8, pp. 1-17.
Losfeld et al., "Design and performance of supported Lewis acid catalysts derived from metal contaminated biomass for Friedel-Crafts alkylation and acylation", Catalysis Today, 2012, vol. 189, pp. 111-116.
Ravindra et al., "Platinum group elements in the environment and their health risk", The Science of the Total Environment, 2004, vol. 318, pp. 1-43.
Kastner et al., "Low Temperature Catalytic Oxidation of Hydrogen Sulfide and Methanethiol Using Wood and Coal Fy Ash", Environ. Sci. Technol., 2003, vol. 37, pp. 2568-2574.
Kolar et al., "Low temperature catalytic oxidation of aldehydes using wood fly ash and molecular oxygen", Applied Catalysis B: Environmental, 2007, vol. 76, pp. 203-217.
Summons to Oral Hearing, dated Apr. 16, 2014, from corresponding EP application.
Summons to Oral Hearing, dated Jun. 18, 2014, from corresponding EP application.
Leonard et al., Tetrahedron 58 (2002) 8373-8397.
International Search Report, dated Mar. 8, 2011, from corresponding PCT application.
A.J.M. Baker et al., "Terrestrial Higher Plants which Hyperaccumulate Metallic Elements—a Review of their Distribution, Ecology and Phytochemistry", Biorecovery, 1989, pp. 81-126, vol. 1; Cited in specification.
Englbert Bauml et al., "Synthesis of Y-Lactones from Alkenes Employing p-Methoxybenzyl Chloride as +CH2-CO2 Equivalent", Tetrahedron Letters, 1988, pp. 6925-6926, vol. 29, No. 52; Cited in specification.
R.R. Brooks, "Chapter three: Geobotany and Hyperaccumulators", Cited in specification.

Michel Darcy, "Zinc Metallurgy/Metallurgie du zinc", Dossier, Techniques de L'Ingenieur, L'Expertise technique et scientifique de reference, 1988; English-language Abstract; Cited in specification.
H. Frerot et al., "Specific interactions between local metallicolous plants improve the phytostabilization of mine soils", Plant and Soil., 2006, pp. 53-65, vol. 282; Cited in specification.
Claude Grison et al., "Thlaspi caerulescens, an indicator of soil pollution?/Thlaspi caerulescens, un indicateur de la pollution d'un sol?", L'actualite chimique, Apr. 2010, pp. 27-32, No. 340; Cited in specification.
Jean Michel Hau, "Metallurgie du zinc", Dossier, Techniques de L'Ingenieur, L'Expertise technique et scientifique de reference.
C. Lievens et al., "Study of the potential valorisation of heavy metal contaminated biomass via phytoremediation by fast pyrolysis: Part 1. Influence of temperature, biomass species and solid heat carrier on the behaviour of heavy metals", Fuel, 2008, pp. 1894-1905, vol. 87; Cited in International Search Report.
Jun Lu et al., "Catalysis of the Biginelli Reaction by Ferric and Nickel Chloride Hexahydrates. One-Pot Synthesis of 3,4-Dihydropyrimidin-2(1H)-ones", Synthesis, 2002, pp. 466-470, No. 4; Cited in specification.
S.P. McGrath et al., "Potential for Phytoextraction of Zinc and Cadmium from Soils Using Hyperaccumulator Plants", 2000.
J. Philibert et al., "Metallurgy from the ore to the material", 2002, pp. 222-227; English-language Abstract; Cited in specification.
Prabha K. Padmavathiamma et al., "Phytoremediation Technology: Hyper-accumulation Metals in Plants", Water Air Soil Pollut, 2007, pp. 105-126, vol. 184; Cited in International Search Report.
R.D. Reeves et al., "European Species of *Thlaspi L.* (*Cruciferae*) as Indicators of Nickel and Zinc", Journal of Geochemical Exploration, 1983, pp. 275-283, vol. 18; Cited in specification.
R.D. Reeves et al., "Hyperaccumulation of Lead and Zinc by Two Metallophytes from Mining Areas of Central Europe", Environmental Pollution (Series A), 1983, pp. 277-285, vol. 31; Cited in specification.
J.P. Rolley et al., "The short story of lead and zinc in the (French region of) Cevennes", 2002, pp. 1-5, Retrieved from the Internet, www.rolley.fr/Geologie/Pb-Zn.html; Cited in specification.
M. Stals et al., "Flash pyrolysis of heavy metal contaminated biomass from phytoremediation: Influence of temperature, entrained flow and wood/leaves blended pyrolysis on the behaviour of heavy metals", Journal of Analytical and Applied Pyrolysis, 2010, pp. 1-7, vol. 87; Cited in International Search Report.
Celine Vidal et al., "*Mesorhizobium metallidurans* sp. nov, a metal-resistant symbiont of *Anthyllis vulneraria* growing on metallicolous soil in Languedoc, France", International Journal of Systematic and Evolutionary Microbiology, 2009, pp. 850-855, vol. 59; Cited in specification.

USE OF METAL-ACCUMULATING PLANTS FOR IMPLEMENTING CHEMICAL REACTIONS

The invention relates to the use of metal-accumulating plants for implementing chemical reactions.

The biological decontamination of soils polluted with metals, metalloids, industrial and agricultural organic waste and effluents or radio-isotopes is an issue of great concern as soil carries out essential functions which largely determine the production of food products and water quality.

Among the different polluting substances, heavy metals belong to the most harmful compounds, as they are not biodegradable and are concentrated in the soils. The example close to Saint Laurent Le Minier (Gard) clearly illustrates the extent of the problem. The exploitation of mineral deposits near Ganges from Roman times until 1992 (Rolley J. P., la petite histoire du plomb et du zinc en Cévennes, www.ensm-ales.fr/~jprolley/Geologie/Pb—Zn.html, 2002), has resulted in significant contamination of the soils with zinc, lead, cadmium (EMETER report, Eléments rares métalliques (ETM) dans le continuum sol-plante, espèces tolérantes et restauration des sites industriels, Contrat Ademe, Coordinator J. Escarré, 2008).

Similar situations are known in Belgium, Luxembourg, in the Jura, the Lower Swiss Alps or in the Pyrenees, to mention only the nearest regions as well as in more distant regions such as New Caledonia where nickel is more particularly exploited.

Technologies for decontaminating soil are difficult to develop, as it is a heterogeneous, complex and dynamic medium which plays a key role as a pollutant buffer and processor.

Different phytoremediation techniques (phytoextraction, phytodegradation, phytostabilization, phytostimulation, phytotransformation, phytovolatilization and rhizofiltration) are currently being developed (Terry, N. and Banuelos G., editors, Phytoremediation of contaminated soil in water, Lewis Publishers, Boca Raton, Fl. 2000).

The Centre d'Ecologie Fonctionnelle et Evolutive (CEFE) and more particularly Doctor Escarré's team is studying the technique of phytostabilization which consists of establishing on contaminated soil plants capable of growing in the presence of heavy metals (the term "tolerance" is used) (Frerot et al., Specific interactions between local metallicolous plants improve the phytostabilization of mine soils, Plant and Soil, 286, 53-65, 2006). Certain of these plant species used have the feature of accumulating large quantities of metals in their vacuoles (the term "hyperaccumulating plants" is used).

The team is quite particularly studying two plants; one of them, *Thlaspi caerulescens* belonging to the Brassicaceae family, possesses remarkable properties of tolerance and hyperaccumulation of zinc, cadmium and nickel. It concentrates them in the above-ground parts (leaves and stems).

This plant is capable of storing zinc at concentrations 100 times greater than that of a standard plant. Moreover, it is capable of extracting and concentrating zinc and cadmium in the above-ground tissues, even on soil having a low concentration of these two metals.

The other plant present in the mining district of Saint Laurent Le Minier, capable of accumulating large quantities of zinc, is *Anthyllis vulneraria*: one of the very rare legumes of the flora of temperate regions to tolerate and accumulate metals. This species has already been used successfully for the phytostabilization of the Aviniéres site at Saint Laurent Le Minier (Frèrot et al., Specific interactions between local metallicolous plants improve the phytostabilization of mine soils, Plant and Soil, 286, 53-65, 2006).

Moreover, it has been shown that if *Anthyllis vulneraria* was also capable of concentrating heavy metals in its above-ground parts, it also played a major role in the phytostabilization of the polluted sites by facilitating the establishment of other plant species. This is due to the ability of *Anthyllis vulneraria* to combine with metallicolous bacteria belonging to the nitrogen-fixing genus *Mesorhizobium* (Vidal et al., *Mesorhizobium metallidurans* sp. nov., a novel metal-resistant symbiont of *Anthyllis vulneraria*, growing on metallicolous soil in Languedoc, France. International Journal of Systematic and Evolutionary Microbiology, in press, 2009).

Given the importance of the biological binding of nitrogen in the rehabilitation of natural environments and more particularly that of polluted environments, the use of a legume is indispensable for rapidly enriching soils with nitrogen.

The presence of *Anthyllis vulneraria* makes it possible to speed up the colonization of these sites by other non-fixing species like grasses such as *Festuca arvernensis*, another species which tolerates but does not accumulate heavy metals.

Beyond their unusual tolerance of $Zn^{2+}$ and $Cd^{2+}$, the hyperaccumulating plants are capable of extracting the metals and transferring them to the above-ground parts where they become concentrated. The roots therefore contain very small amounts of heavy metals, unlike the non-accumulating plant species. This three-fold property of tolerance/accumulation/concentration in the harvestable parts makes them an appropriate phytoremediation tool.

However, there are still certain problems to be solved in order to go beyond the scope of simple stabilization of polluted sediments and hope to develop phytoextraction on a large scale. The valorization of biomass enriched with heavy metals is still to be developed, as at present, only transfer of the metals from the soil to the plant is carried out. The metals are not removed from the site.

Moreover, the heavy metals are commonly used in organic chemistry as catalysts indispensable for carrying out chemical transformations requiring significant activation energy. The role of the catalysts is then to lower the energy barrier.

Their operating method is frequently based on their Lewis acid properties. Zinc chloride is among the most used and is indispensable in numerous industrial and laboratory reactions. It is also frequently used in heterocyclic organic chemistry for catalyzing numerous electrophilic aromatic substitutions.

It is also a catalyst of choice for carrying out the hydrogenation of primary alcohols with Lucas's reagent, acetalization, aldolization reactions or Diels-Alder type cycloaddition reactions etc.

They are also very useful in analytical electrochemistry, electrometallurgy and liquid-solid extraction where the fields of application are numerous and directly involved in different areas of economic life (batteries, fuel cells and accumulators, detectors of spectroscopic equipment, metallurgy, welding etc.)

Their production is based on extractive metallurgical processes starting from minerals.

Two processes are possible (Darcy M., Métallurgie du zinc, 1988, editions techniques de l'ingénieur; Philibert J. et al., Métallurgie du minerai au matériau, Editions Dunod, $2^{nd}$ edition, 2002):

pyrometallurgy which requires successive heat treatments which can exceed 1000° C., hydrometallurgy which is based on strong acid treatments followed by electrolysis with high electrical energy consumption. It also has an environmental impact by discharging polluted effluents.

The diversity of the minerals does not allow for single processes. A good number of them require intermediate liquid-liquid extraction phases, which inevitably results in the use of organic solvents which are harmful to the environment and high extraction costs.

One of the aspects of the invention relates to the use of metal catalysts originating from heavy metal-accumulating plants avoiding the use of organic solvents which are harmful to the environment and the discharge of polluted effluents, and allowing the removal of the heavy metals from the sites polluted by them and the valorization of the biomass containing them.

Another aspect consists of providing a process for producing said catalysts.

Another aspect consists of providing chemical processes utilizing such catalysts.

A last aspect consists of providing compositions containing said catalysts.

The present invention relates to the use of a calcined plant or calcined plant part having accumulated at least one metal in the M(II) form chosen in particular from zinc (Zn), nickel (Ni) or copper (Cu), for the preparation of a composition containing at least one metal catalyst the metal of which is one of the aforesaid metals in the M(II) form originating from said plant, said composition being devoid of chlorophyll, and allowing the implementation of organic synthesis reactions involving said catalyst.

The expression "calcined plant or calcined plant part having accumulated at least one metal>> firstly denotes all the above-ground parts (leaves, stems etc.) of the plant in which the metals, previously present in a soil contaminated with them, have accumulated, i.e. have been stored, in particular in the vacuoles of the plants, for example in the form of metal carboxylates, in particular predominantly metal malate, but also citrate, succinate and oxalate. They can also be stored combined with amino acids of chelating proteins, phytochelatines or metallothioneins.

The term "calcined" denotes a heat treatment of the plant, in particular from 200° C. to 400° C., in particular 300° C., making it possible to dehydrate the plant and to at least partially destroy the organic matter and thus release the metal or the metals contained in the plant.

The dehydration and the at least partial destruction of the organic matter can also be achieved by dehydration in an oven at a lower temperature, from 50° C. to 150° C., in particular 100° C. but leads to a composition the metal content of which is different (Example 1).

The term metal must be interpreted in a broad sense and denotes metals such as zinc, copper, nickel, iron, chromium, manganese, cobalt, aluminium, lead, cadmium, arsenic, thallium or palladium but also alkaline-earth metals such as magnesium or calcium or alkali metals such as sodium or potassium.

Said metals are mainly in the cationic form.

The expression "in the M(II) form" means that the metal has an oxidation number equal to 2.

However, the composition can also contain one or more metals in another form, i.e. with a different oxidation number, in particular an oxidation number equal to 3 or 1.

In the remainder of the description, the plant or plant parts can also be called vegetable matter or biomass and have the same meaning.

It can however also denote the underground parts of the plant such as the roots.

By the expression "metal catalyst", is meant a compound comprising a metal, preferably in the M(II) form, combined with a counter-ion and which, after utilization in an organic synthesis reaction, will be recovered in the same form as when it was reacted and can therefore be recycled for the same organic synthesis reaction or for a different organic synthesis reaction.

The catalyst can also have a different oxidation number.

The expression "originating from said plant" means that the metal or the metals present in the composition of the invention originate from the plant before calcination and that there has been no addition of metal obtained from an origin other than said plant after calcination, acid treatment or filtration.

Metals such as zinc, copper, nickel, aluminium, cobalt, lead, chromium, manganese, arsenic or thallium have been accumulated by the plant during its growth in a soil containing said species.

Conversely, other cationic species such as $Mg^{2+}$, $Ca^{2+}$, $Fe^{3+}$, $Na^+$ and $K^+$ have therefore not been accumulated by said plant but are physiologically present in said plant and consequently originate from the latter.

With respect to $Fe^{3+}$, the soil can also contain significant concentrations of this metal ion which pollutes the foliar mass and therefore also originates from the plant.

Conversely, it is also possible to add a metal which would originate from the calcination of another plant having accumulated one or more metals, from a catalytic support or metal dust originating from the harvest environment.

The expression "devoid of chlorophyll" means that the composition no longer contains chlorophyll or contains only residues or traces thereof due to the different treatments carried out during the preparation of the composition and in particular, filtration after acid treatment.

The acid treatment carried out after calcination makes it possible to completely destroy the organic matter present in the plant from which it originates.

Filtration makes it possible to remove the residues of organic matter and in particular the chlorophyll or the residues of chlorophyll which could remain after acid treatment.

By the expression "implementation of an organic synthesis reaction involving the latter", is meant the transformation of a product X to product Y using the catalyst and optionally one or more other products.

The metal is preferably zinc (Zn) nickel (Ni) or copper (Cu) but it can also be cadmium (Cd), lead (Pb), arsenic (As), cobalt (Co) or chromium (Cr), manganese (Mn) or thallium (Tl), iron (Fe), calcium (Ca), magnesium (Mg), sodium (Na(I)), potassium (K(I)) or aluminium (III).

One of the advantages of the invention is therefore the removal of the heavy metals present in the polluted sites and valorization of the biomass containing said heavy metals while providing a source of metals for organic synthesis reactions, avoiding the use of process with a high consumption of energy and organic solvents which are harmful to the environment as well as the discharge of polluted effluents.

Another advantage is the possibility of using the composition containing the catalyst for reactions in an industrial environment.

In an advantageous embodiment, the present invention relates to the use of a calcined plant or a calcined plant part having accumulated at least one metal in the M(II) form and at least one metal in the M(III) form, said metal in the M(II) form being chosen in particular from zinc (Zn), nickel (Ni) or copper (Cu), for the preparation of a composition containing at least one metal catalyst the metal of which is one of the aforesaid metals in the M(II) form originating from said plant, said composition being devoid of chlorophyll, and allowing the implementation of organic synthesis reactions involving said catalyst.

In an advantageous embodiment, the invention relates to the use of a calcined plant or a calcined plant part having accumulated at least one metal in the M(II) form chosen in particular from zinc (Zn), nickel (Ni) or copper (Cu) as defined above, in which said composition is devoid of activated carbon.

The expression "devoid of activated carbon" means that the composition contains no carbon having a large specific surface area giving it a high absorption capacity.

For active carbon, the specific surface area is from 500 to 2500 $m^2/g$.

In the remainder of the description, the expression "active carbon" can also be used and has the same meaning as the expression "activated carbon".

In an advantageous embodiment, the invention relates to the use of a calcined plant or a calcined plant part having accumulated at least one metal in the M(II) form chosen in particular from zinc (Zn), nickel (Ni) or copper (Cu) as defined above, in which said composition comprises less than approximately 2%, in particular less than approximately 0.2% by weight of C, in particular approximately 0.14%.

The calcination of said plant leads not only to the destruction of the organic matter but also to the conversion of the carbon thus formed to $CO_2$ which will therefore be almost completely removed from the composition.

In an advantageous embodiment, the invention relates to the use of a calcined plant or a calcined plant part having accumulated at least one metal in the M(II) form chosen in particular from zinc (Zn), nickel (Ni) or copper (Cu) as defined above, in which the acid treatment is carried out by hydrochloric acid, in particular gaseous HCl, 1N HCl or 12N HCl, or sulphuric acid.

In an advantageous embodiment, the invention relates to the use of a calcined plant or a calcined plant part as defined above, in which said at least one metal in the M(II) form is chosen from zinc (Zn), nickel (Ni), manganese (Mn), lead (Pb), cadmium (Cd), calcium (Ca), magnesium (Mg) or copper (Cu), for the preparation of a composition containing at least one active metal catalyst, in the M(II) form originating from said plant, said composition having been previously filtered, after acid treatment, in order to remove the chlorophyll, thus allowing the implementation of organic synthesis reactions involving said catalyst.

A plant is capable of accumulating or containing one or more metals and as a result the composition can comprise a metal chosen from: Zn, Ni, Mn, Na(I), K(I), Pb, Cd, Ca, Mg, Co, As or Cu.

It can also comprise iron which is originally present in the M(III) form but which after reduction, is present only in the M(II) form.

It can moreover comprise aluminium which is present in the M(III) form.

Throughout the description, when the oxidation number of the M(I), M(II) or M(III) metal is not specified, it is the M(II) form.

The composition can comprise two metals chosen from those mentioned above.

The composition can comprise three metals chosen from those mentioned above.

The composition can comprise four metals chosen from those mentioned above.

The composition can comprise five metals chosen from those mentioned above.

The composition can comprise six metals chosen from those mentioned above.

The composition can comprise seven metals chosen from those mentioned above.

The composition can comprise eight metals chosen from those mentioned above.

The composition can comprise nine metals chosen from those mentioned above.

The composition can comprise ten metals chosen from those mentioned above.

The composition can comprise eleven metals from those mentioned above.

The composition can comprise twelve metals from those mentioned above.

The composition can comprise thirteen metals from those mentioned above.

The composition can comprise the fourteen metals mentioned above.

In an advantageous embodiment, the invention relates to the use of a calcined plant or a calcined plant part having accumulated at least one metal in the M(II) form chosen in particular from zinc (Zn), nickel (Ni) or copper (Cu), as defined above, in which the filtered composition is optionally subsequently purified.

It can be beneficial, depending on the organic reactions to be carried out, to at least partially purify the composition after filtration so as to enrich it with one or more metal species which are favourable to said organic reaction. However, the reaction also occurs without purification, which makes purification optional.

In an advantageous embodiment, the invention relates to the use of a calcined plant or a calcined plant part having accumulated at least one metal in the M(II) form chosen in particular from zinc (Zn), nickel (Ni) or copper (Cu) as defined above, in which said plant is chosen from the Brassicaceae family, in particular the species of the genus *Thlaspi* in particular *T. caerulescens, T. goesingense, T. tatrense, T. rotundifolium, T. praecox*, the species of the genus *Arabidopsis*, in particular *Arabidopsis hallerii*, and of the genus *Alyssum*, in particular *A. bertolonii, A. serpyllifolium*, the Fabaceae, in particular *Anthyllis vulneraria*, the Sapotaceae, in particular the species *Sebertia acuminata, Planchonella oxyedra*, the Convolvulaceae, in particular the species *Ipomea alpina, Planchonella oxyedra*, o the Rubiaceae, in particular the species *Psychotria douarrei*, in particular *P. costivenia, P. clementis, P. vanhermanii*, the Cunoniaceae, in particular the *Geissois*, the Scrophulariaceae, in particular the species of the genus *Bacopa*, in particular *Bacopa monnieri*, the algae, in particular the red algae, in particular the rhodophytes, more particularly *Rhodophyta bostrychia*, the green algae or the brown algae.

Not all the plants belonging to the families of the Brassicaceae, Fabaceae, Sapotaceae, Convolvulaceae or Rubiaceae are capable of growing on soil containing heavy metals and accumulating said heavy metals in the above-ground parts.

As a result, in the Brassicaceae family, the genera *Thlaspi, Arabidopsis* and *Alyssum* are the preferred genera but without being limited thereto.

In the Fabaceae family, *Anthyllis vulneraria* is preferred but also without being limited thereto.

In the Sapotaceae family, the species *Sebertia acuminata*, *Planchonella oxyedra* are the preferred species but without being limited thereto.

In the Convolvulaceae family, the species *Ipomea alpina*, *Planchonella oxyedra* are the preferred species but without being limited thereto.

In the Rubiaceae family, the species *Psychotria douarrei*, in particular *P. costivenia, P. clementis, P. vanhermanii* are preferred but without being limited thereto.

In the Scrophulariaceae family, the species *Bacopa monnieri* is preferred but without being limited thereto.

Finally, in the algae, *Rhodophyta bostrychia* is the preferred species but without being limited thereto.

Table I below shows the different genera, without being limited thereto, capable of accumulating metals such as nickel, zinc, cobalt and copper, lead, chromium, manganese or thallium.

Each genus is obviously capable of accumulating the metal mentioned and optionally one or more others, in particular cadmium or aluminium(III).

TABLE I

Compilation based on:
AJM Baker & R R Brooks 1989. Terrestrial higher plants which hyperaccumulate metallic elements - A review of their distribution, ecology and phytochemistry. Biorecovery, 1, 81-126;
Brooks, R R (editor). 1998. Plants that hyperaccumulate heavy metals. Cabi Publishing. Wallingford. U.K.

| NICKEL | ZINC | COBALT & COPPER | LEAD | CHROMIUM |
|---|---|---|---|---|
| *Adiantum* | *Arabidopsis* | *Aeollanthus* | *Armeria* | *Dicoma* |
| *Agatea* | *Arenaria* | *Alectra* | *Polycarpaea* | *Sutera* |
| *Alyssum* | *Cardaminopsis* | *Anisopappus* | *Thlaspi* | |
| *Anthyllis* | *Haumaniastrum* | *Ascolepis* | *Noccaea* | |
| *Arenaria* | *Noccaea* | *Bacopa* | *Alyssum* | |
| *Argophyllum* | *Silene* | *Becium* | | |
| *Baloghia* | *Thlaspi* | *Buchnera* | MANGANESE | |
| *Berkheya* | *Viola* | *Bulbostylis* | | |
| *Blepharis* | | *Celosia* | *Alyxia* | |
| *Bornmuellera* | | *Commelina* | *Beaupreopsis* | |
| *Brackenridgea* | | *Crassula* | *Crotalaria* | |
| *Buxus* | | *Crotalaria* | *Grevilla* | |
| *Campanula* | | *Cyanotis* | *Eugenia* | |
| *Cardamine* | | *Eragrostis* | *Macadamia* | |
| *Casearia* | | *Faroa* | *Maytenus* | |
| *Chromolaena* | | *Gutenbergia* | *Virotia* | |
| *Chrysanthemum* | | *Haumaniastrum* | | |
| *Cleidion* | | *Hibiscus* | THALLIUM | |
| *Cnidoscolus* | | *Icomum* | *Iberis* | |
| *Cochlearia* | | *Ipomoea* | | |
| *Dicoma* | | *Lindernia* | ALUMINIUM | |
| *Dychapetalum* | | *Millotia* | *Melastoma* | |
| *Esterhazya* | | *Minuartia* | *Psychotria* | |
| *Euphorbia* | | *Monadenium* | *Symplocos* | |
| *Geissois* | | *Pandiaka* | | |
| *Heliotropium* | | *Rendlia* | | |
| *Homalium* | | *Silene* | | |
| *Hybanthus* | | *Sopubia* | | |
| *Indigofera* | | *Striga* | | |
| *Juncus* | | *Triumfetta* | | |
| *Justicia* | | *Vernonia* | | |
| *Lasiochlamys* | | *Vigna* | | |
| *Leucanthemopsis* | | *Xerophyta* | | |
| *Leucocroton* | | | | |
| *Linaria* | | | | |
| *Lophostachys* | | | | |
| *Luzula* | | | | |
| *Merremia* | | | | |
| *Minuartia* | | | | |
| *Mitracarpus* | | | | |
| *Myristica* | | | | |
| *Noccaea* | | | | |
| *Oncotheca* | | | | |
| *Pancheria* | | | | |
| *Pearsonia* | | | | |
| *Peltaria* | | | | |
| *Phyllanthus* | | | | |
| *Planchonella* | | | | |
| *Psychotria* | | | | |
| *Rhus* | | | | |
| *Rinorea* | | | | |
| *Ruellia* | | | | |
| *Saxifraga* | | | | |
| *Sebertia* | | | | |
| *Senecio* | | | | |

TABLE I-continued

Compilation based on:
AJM Baker & R R Brooks 1989. Terrestrial higher plants which hyperaccumulate metallic elements - A review of their distribution, ecology and phytochemistry. Biorecovery, 1, 81-126;
Brooks, R R (editor). 1998. Plants that hyperaccumulate heavy metals. Cabi Publishing. Wallingford. U.K.

| NICKEL | ZINC | COBALT & COPPER | LEAD | CHROMIUM |
|---|---|---|---|---|
| *Shorea* | | | | |
| *Solidago* | | | | |
| *Stachys* | | | | |
| *Stackhousia* | | | | |
| *Streptanthus* | | | | |
| *Thlaspi* | | | | |
| *Trichospermum* | | | | |
| *Trifolium* | | | | |
| *Trisetum* | | | | |
| *Turnera* | | | | |
| *Vellozia* | | | | |
| *Walsura* | | | | |
| *Xylosma* | | | | |

In an advantageous embodiment, the invention relates to the use of a calcined plant or a calcined plant part having accumulated at least one metal in the M(II) form chosen in particular from zinc (Zn), nickel (Ni) or copper (Cu) as defined above, in which said plant belongs to the Brassicaceae family, in particular *Thlaspi caerulescens* or *Arabidopsis hallerii* and the metal accumulated by said plant is Zn.

In this embodiment, the plants used are advantageously *Thlaspi caerulescens* or *Arabidopsis hallerii* which all accumulate predominantly zinc, in particular in the form of zinc carboxylate (in particular malate), i.e. in the $Zn^{2+}$ (or Zn(II)) form as well as other metals in a lower proportion.

The zinc catalyst can be obtained for example according to Example 1. In this case, the catalyst obtained is a Lewis acid corresponding to zinc dichloride.

One of the advantages of the invention is therefore the provision of a catalyst not requiring thorough purification. In fact, the presence of the other metal salts (such as for example $CdCl_2$ or others) will not interfere with the organic reactions implemented and it is therefore not necessary as in the standard processes to carry out a complete and difficult separation of the metal species present.

In an advantageous embodiment, the invention relates to the use of a calcined plant or a calcined plant part having accumulated at least one metal in the M(II) form, in particular zinc, as defined above, in which the Zn concentration in the plant comprises approximately 2700 mg/kg to approximately 43700 mg/kg of dry weight of plant or plant part, preferably from approximately 2700 mg/kg to approximately 13600 mg/kg of dry weight of plant or plant part, more preferably from approximately 6000 mg/kg to approximately 9000 mg/kg of dry weight of plant or plant part, in particular of approximately 7000 mg/kg to approximately 8000 mg/kg of dry weight of plant or plant part.

Below 2700 mg/kg, the proportion of zinc is too low to be able to valorize the biomass containing zinc at reasonable cost.

Beyond 43700 mg/kg, the proportion of zinc is too high for the plant to be able to store so much metal.

The concentrations present in the plant can differ widely depending on the nature of the substrate and the quantity of metals in the soil.

To be precise, the results obtained on 24 *Thlaspi* plants harvested on the mine sites are as follows: the average was 7300 mg/kg with a standard deviation of 3163, a maximum value of 13600 and a minimum of 2700.

In hydroponic culture, in which plants are grown on a neutral and inert substrate (such as sand, pozzolan, clay beads, nutrient solution etc.), the values can be much higher of the order of 30000 mg/kg (up to 43710 mg/kg according to Brooks and Reeves).

Reeves, R. D. and Brooks, R. R., 1983. European species of *Thlaspi* L. (Cruciferae) as indicators of nickel and zinc. *J. Geochem. Explor.* 18:275-283. Reeves, R. D. and Brooks, R. R., 1983. Hyperaccumulation of lead and zinc by two metallophytes from a mining area in Central Europe. *Environ. Pollut.* 31:277-287.

In an advantageous embodiment, the invention relates to the use of a calcined plant or a calcined plant part having accumulated at least one metal in the M(II) form, in particular zinc, for the preparation of a composition as defined above, in which the zinc in said composition is at a concentration comprised from approximately 15000 to approximately 800000 ppm, in particular from approximately 20000 to approximately 80000 ppm, in particular from approximately 61000 to approximately 67700 ppm.

The catalyst obtained is therefore a zinc catalyst, i.e. zinc is the only metal compound present in the composition or the main metal compound in the composition.

By ppm, also used throughout the remainder of the description, is meant mg/kg.

Given that for the same plant, a seasonable variability can exist, consequently modifying the concentration of metals in the plant and as a result in the composition and that, moreover, the determination of the values of concentrations of the metals can vary as a function of the measurement, the values of the ranges of concentrations are given throughout the description with a margin of error of plus or minus 8%, preferably of plus or minus 7%, in particular a standard error of plus or minus 5%.

In an advantageous embodiment, the invention relates to the use of a calcined plant or a calcined plant part having accumulated at least one metal in the M(II) form, in particular zinc, as defined above, in which said composition also comprises at least one of the following metals: Mg, Al(III), Ca, Fe(III), Cu, Cd, Pb, at the concentrations defined above.

In an advantageous embodiment, the invention relates to the use of a calcined plant or a calcined plant part having accumulated at least one metal in the M(II) form, in particular zinc, as defined above, in which the zinc in the composition is at a concentration comprised from approximately 15000 to approximately 800000 ppm, in particular from approximately 20000 to approximately 80000 ppm, in particular from approximately 61000 to approximately 67700 ppm, said composition also comprising one or more metals from the following list at the following concentrations:

Mg(II): from approximately 2500 to approximately 25000 ppm, in particular from approximately 4400 to approximately 15000 ppm, in particular from approximately 11800 to approximately 13100 ppm;

Ca(II): from approximately 20000 to approximately 100000 ppm, in particular from approximately 73000 to approximately 91000 ppm;

Fe(III): from approximately 900 to approximately 75000 ppm, in particular from approximately 3100 to approximately 30000 ppm, in particular from approximately 8700 to approximately 28000 ppm;

Cu(II): from approximately 30 to approximately 400 ppm, in particular from approximately 55 to approximately 170 ppm, in particular from approximately 99 to approximately 170 ppm;

Cd(II): from approximately 700 to approximately 10000 ppm, in particular from approximately 1800 to approximately 5600 ppm, in particular from approximately 5300 to approximately 5600 ppm;

Pb(II): from approximately 200 to approximately 40000 ppm, in particular from approximately 4600 to approximately 15000 ppm, in particular from approximately 13000 to approximately 15000 ppm;

Al(III): from approximately 200 to approximately 15000 ppm, in particular from approximately 2400 to approximately 6000 ppm, in particular from approximately 1500 to approximately 4700 ppm;

The metal contents depend not only on the plant used but also on the place in which said plant has been cultivated and in particular on the metal content of the soil.

This is why the ranges of metals accumulated in the plant can be very wide.

In an advantageous embodiment, the invention relates to the use of a calcined plant or a calcined plant part having accumulated at least one metal in the M(II) form, in particular zinc, as defined above, in which said composition comprises at least the following metals: Mg, Al(III), Ca, Fe(III), Cu, Zn, Cd, Pb, at the concentrations defined above.

In an advantageous embodiment, the invention relates to the use of a calcined plant or a calcined plant part having accumulated at least one metal in the M(II) form, as defined above, in which said plant is a Sapotaceae, in particular *Sebertia acuminata*, a Rubiaceae, or a Brassicaceae, in particular *Thlaspi goesingense* or *Thlaspi caerulescens*, and the metal accumulated by said plant is Ni.

In this embodiment, the plants used are advantageously *Sebertia acuminata, Thlaspi caerulescens* or *Thlaspi goesingense* as well as a Rubiaceae which all accumulate predominantly nickel, in particular in the form of nickel carboxylate, i.e. in the $Ni^{2+}$ form as well as other metals in a lower proportion.

The nickel catalyst can be obtained for example according to Example 5. In this case, the catalyst obtained is a Lewis acid corresponding to nickel chloride.

In an advantageous embodiment, the invention relates to the use of a calcined plant or a calcined plant part having accumulated at least one metal in the M(II) form, in particular nickel, as defined above, in which the Ni concentration in the plant comprises approximately 1000 mg/kg to approximately 36000 mg/kg of dry weight of plant or plant part, preferably from approximately 2500 mg/kg to approximately 25000 mg/kg of dry weight of plant or plant part, more preferably from approximately 2500 mg/kg to approximately 19900 mg/kg of dry weight of plant or plant part, in particular from approximately 15000 mg/kg to approximately 18000 mg/kg of dry weight of plant or plant part Below 1000 mg/kg, the proportion of nickel is too low to be able to valorize the biomass containing nickel at reasonable cost.

Beyond 36000 mg/kg, the proportion of nickel is too high for the plant to be able to store so much metal.

The concentrations present in the plant can differ widely depending on the nature of the substrate and the quantity of metals in the soil.

In hydroponic culture, in which plants are grown on a neutral and inert substrate (such as sand, pozzolan, clay beads, nutrient solution etc.), the values can be much higher, of the order of 36000 mg/kg.

In an advantageous embodiment, the invention relates to the use of a calcined plant or a calcined plant part having accumulated at least one metal in the M(II) form, in particular nickel, for the preparation of a composition as defined above, in which the nickel in said composition is at a concentration comprised from approximately 150000 to approximately 700000 ppm, in particular from approximately 185000 to approximately 300000 ppm, in particular from approximately 185000 to approximately 270000 ppm.

The catalyst obtained is therefore a nickel catalyst, i.e. nickel is the only metal compound present in the composition or the main metal compound in the composition.

In an advantageous embodiment, the invention relates to the use of a calcined plant or a calcined plant part having accumulated at least one metal in the M(II) form, in particular nickel, as defined above, in which the nickel in the composition is at a concentration comprised from approximately 150000 to approximately 700000 ppm, in particular from approximately 185000 to approximately 300000 ppm, in particular from approximately 185000 to approximately 270000 ppm, said composition also comprising one or more metals from the following list at the following concentrations:

Mg(II): from approximately 9000 to approximately 100000 ppm, in particular from approximately 50000 to approximately 90000 ppm, in particular from approximately 78000 to approximately 87000 ppm;

Ca(II): from approximately 60000 to approximately 120000 ppm, in particular from approximately 93000 to approximately 106000 ppm;

Zn(II): from approximately 5000 to approximately 8000 ppm, in particular from approximately 5700 to approximately 7100 ppm;

Fe(III): from approximately 200 to approximately 2000 ppm, in particular from approximately 260 to approximately 1800 ppm;

Cu(II): from approximately 4000 to approximately 5000 ppm, in particular from approximately 4500 to approximately 4700 ppm;

Cd(II): from approximately 10 to approximately 40 ppm, in particular from approximately 14 to approximately 20 ppm;

Pb(II): from approximately 200 to approximately 1500 ppm, in particular from approximately 300 to approximately 1200 ppm;

Al(III): from approximately 600 to approximately 2000 ppm, in particular from approximately 800 to approximately 1700 ppm;

Mn(II): from approximately 100 to approximately 1500 ppm, in particular from approximately 260 to approximately 1200 ppm;

In an advantageous embodiment, the invention relates to the use of a calcined plant or a calcined plant part having accumulated at least one metal in the M(II) form, in particular nickel, as defined above, in which said composition comprises at least the following metals: Mg, Al(III), Ca, Fe(III), Cu, Zn, Cd, Pb, Ni, Mn at the concentrations defined above.

In an advantageous embodiment, the catalyst based on $NiCl_2$ is used for carrying out a reaction in which a Lewis acid such as $NiCl_2$ is used, such as an alkylating (see Example 11) or acylating electrophilic substitution reaction.

In an advantageous embodiment, the invention relates to the use of a calcined plant or a calcined plant part having accumulated at least one metal in the M(II) form chosen in particular from zinc (Zn), nickel (Ni) or copper (Cu), as defined above, in which said plant is a Convolvulaceae, in particular *Ipomea alpina* or *Bacopa monnieri* and the metal accumulated by said plant is Cu.

In this embodiment, the plant used is advantageously *Ipomea alpina* or *Bacopa monnieri*, which all accumulate predominantly copper, i.e. in the $Cu^{2+}$ form as well as other metals in a lower proportion.

The copper catalyst can be obtained for example according to Example 9. In this case, the catalyst obtained is a Lewis acid corresponding to cupric chloride.

In an advantageous embodiment, the invention relates to the use of a calcined plant or a calcined plant part having accumulated at least one metal in the M(II) form chosen in particular from zinc (Zn), nickel (Ni) or copper (Cu), in particular of copper, as defined above, in which the Cu concentration in the plant is comprised from approximately 1000 mg/kg to approximately 13700 mg/kg of dry weight of plant or plant part.

Below 1000 mg/kg, the proportion of copper is too low to be able to valorize the biomass containing the copper at reasonable cost.

Beyond 13700 mg/kg, the proportion of copper is too high for the plant to be able to store so much metal.

The concentrations present in the plant can differ widely depending on the nature of the substrate and the quantity of metals in the soil.

In hydroponic culture, in which plants are grown on a neutral and inert substrate (such as sand, pozzolan, clay beads, nutrient solution etc.), the values can be much higher, of the order of 36000 mg/kg.

In an advantageous embodiment, the invention relates to the use of a calcined plant or a calcined plant part having accumulated at least one metal in the M(II) form, in particular copper, for the preparation of a composition as defined above, in which the copper in said composition is at a concentration comprised from approximately 6000 to approximately 60000 ppm, in particular from approximately 10000 to approximately 30000 ppm.

The catalyst obtained is therefore a copper catalyst, i.e. copper is the only metal compound present in the composition or the main metal compound in the composition.

In an advantageous embodiment, the invention relates to the use of a calcined plant or a calcined plant part having accumulated at least one metal in the M(II) form, in particular copper, as defined above, in which the copper in the composition is at a concentration comprised from approximately 6000 to approximately 60000 ppm, in particular from approximately 10000 to approximately 30000 ppm, said composition also comprising one or more metals from the following list at the following concentrations:

Mg(II): from approximately 6000 to approximately 10000 ppm, in particular from approximately 7000 to approximately 9000 ppm;

Ca(II): from approximately 70000 to approximately 150000 ppm, in particular from approximately 90000 to approximately 140000 ppm;

Zn(II): from approximately 1000 to approximately 4000 ppm, in particular from approximately 1500 to approximately 3400 ppm;

Fe(III): from approximately 3000 to approximately 8000 ppm, in particular from approximately 4100 to approximately 5700 ppm;

Cd(II): from approximately 300 to approximately 600 ppm, in particular from approximately 380 to approximately 520 ppm;

Pb(II): from approximately 800 to approximately 2000 ppm, in particular from approximately 1000 to approximately 1500 ppm;

Al(III): from approximately 1800 to approximately 6500 ppm, in particular from approximately 2100 to approximately 5500 ppm;

In an advantageous embodiment, the invention relates to the use of a calcined plant or a calcined plant part having accumulated at least one metal in the M(II) form, in particular copper, as defined above, in which said composition comprises at least the following metals: Mg, Al(III), Ca, Fe(III), Cu, Zn, Cd, Pb, Ni, at the concentrations defined above.

In an advantageous embodiment, the invention relates to the use of a calcined plant or a calcined plant part having accumulated at least one metal in the M(II) form, as defined above, in which the composition after filtration is utilized without subsequent purification in organic synthesis reactions chosen from the halogenations in particular of alcohols, electrophilic aromatic reactions in series, in particular substitutions, the synthesis of 3,4-dihydropyrimidin-2(1H)-one (or thione), cycloaddition reactions, transesterification reactions, catalyst synthesis reactions for coupling or hydrogenation reactions after reduction of Ni(II) to $Ni^0$, the synthesis of amino acid or oxime developers, and the catalyzed hydrolysis of the sulphur-containing organic functions in particular the thiophosphates.

In this embodiment, the catalyst containing mainly zinc, or copper or nickel is used without purification, i.e. as obtained after acid treatment and filtration and makes it possible to carry out several types of organic reactions.

By halogenation of alcohols, also called Lucas reaction, is meant the transformation of alcohols (R—OH), whether primary, secondary or tertiary, to a corresponding halogenated derivative (R-Hal), in particular to R—Cl, catalyzed by a zinc catalyst.

By "electrophilic aromatic substitution in series", is meant a reaction during which an atom, generally hydrogen, bound to an aromatic ring is substituted by an electrophilic group: ArH+EX→ArE+HX, also catalyzed by a zinc or nickel catalyst.

(see for example Example 11)

As stated above, the catalyst can be recycled several times, in particular at least four times, and by way of example, the zinc catalyst was recycled 4 times in the electrophilic aromatic substitutions without any loss of activity.

It is also possible to carry out electrophilic addition reactions where $ZnCl_2$ catalyzes the reaction of p-methoxybenzyl chloride with alkenes in order to produce the corresponding 1:1 addition products (Bäuml, E., Tscheschlok, K.; Pock, R. and Mayr, H., 1978. Synthesis of γ-lactones from alkenes employing p-methoxybenzyl chloride as $^+CH_2$—$CO^-_2$ equivalent, *Tetrahedron Lett.* 29: 6925-6926).

The synthesis of 3,4-dihydropyrimidin-2(1H)-one (or thione), or Biginelli reaction, corresponds to the reaction of an aromatic aldehyde with a urea or a thiourea and an alkyl acetoacetate. It can be catalyzed just as well by the zinc catalyst as the nickel catalyst.

The cycloaddition reactions, also called Diels-Alder reaction, correspond to the addition of a diene to a dienophile and are catalyzed by a zinc or nickel catalyst.

The transesterification reactions correspond to the replacement of one alkyl ester, for example methyl, ethyl, propyl, etc. by another, by treatment of the ester with an alcohol different from that constituting the ester. They are catalyzed by the zinc catalyst.

In the coupling or hydrogenation reactions, the nickel catalyst obtained above, for example $NiCl_2$, is reduced beforehand by the standard techniques well known to a person skilled in the art—for example to $Ni^0$ according to Example 7.

Said catalyst combined with phosphorus-containing ligands (see Example 6), then reduced can then be used to carry out coupling reactions such as the synthesis of biaryls or hydrogenation reactions for example of alkenes and/or nitro groups with Raney nickel (see for example Example 8), or carbonylated derivatives, alkynes and aromatic compounds.

The catalyst based on $CuCl_2$ is used for implementing a reaction in which a Lewis acid such as $CuCl_2$ is used, such as an alkylating electrophilic substitution reaction (see Example 11).

The synthesis of amino acid or oxime developers corresponds to the use of the copper catalyst to develop chemical compounds such as amino acids or oximes (see for example Example 10).

The catalyzed hydrolysis of thiophosphates corresponds in particular to the detoxification of a pesticide called parathion from the organophosphate family, which has proved toxic to plants, animals and humans.

Said hydrolysis is preferably catalyzed by the copper catalyst but can also be carried out by the zinc catalyst.

In an advantageous embodiment, the invention relates to the use of a calcined plant or calcined plant part having accumulated at least one metal in the M(II) form, as defined above, in which the composition after filtration is purified before use in organic synthesis reactions chosen from the halogenations in particular of alcohols, electrophilic aromatic reactions in series, in particular substitutions, the synthesis of 3,4-dihydropyrimidin-2(1H)-one (or thione), cycloaddition reactions, transesterification reactions, catalyst synthesis reactions for coupling or hydrogenation reactions after reduction of Ni(II) to $Ni^0$, the synthesis of amino acid or oxime developers, and the catalyzed hydrolysis of thiophosphates.

In this embodiment, the catalyst containing predominantly zinc, or copper or nickel is used after purification, i.e. such as after acid treatment and filtration, it can undergo various purifications making it possible to enrich it with a metal, in particular zinc and/or iron(III) or iron(II) and makes it possible to carry out the same organic reactions as defined above but improving the yield and/or increasing the rate of certain reactions, in particular transesterification reactions, 3,4-dihydropyrimidin-2(1H)-one (or thione) synthesis reactions, cycloaddition reactions or halogenation reactions, in particular of alcohols.

In an advantageous embodiment, the invention relates to the use of a calcined plant or calcined plant part having accumulated at least one metal in the M(II) form as defined above, in which the purification of the composition leads to a composition enriched with zinc and/or iron(III), said purification being carried out according to a method chosen from: an ion exchange resin, liquid-liquid extraction with trioctylamine, selective precipitation, in particular with NaF or as a function of the pH, liquid/solid extraction by washing with acetone.

Ion exchange resins, well known to a person skilled in the art, in particular cation exchange resins and in particular Amberlyte resin IRA400, make it possible to retain certain metals such as zinc and/or iron(III) while the other cationic species that may be present in the composition are eluted. After rinsing in an acid medium, in particular with 0.5M HCl, iron(III) is eluted and zinc is detached from the resin, for example after stifling the resin for 12 to 24 hours at a temperature comprised between 10 and 30° C., preferably at ambient temperature, in an acid medium, in particular 0.005N HCl.

The zinc-enriched composition obtained after treatment with the ion exchange resin comprises a concentration of zinc comprised from approximately 600000 to approximately 800000 ppm, in particular approximately 705000 ppm, and optionally one or more metals chosen from the following at the following concentrations:

Mg(II): from approximately 10000 to approximately 15000 ppm, in particular approximately 14000 ppm;
Ca(II): from approximately 15000 to approximately 25000 ppm, in particular approximately 20100 ppm;
Fe(III): from approximately 2200 to approximately 3000 ppm, in particular approximately 2650 ppm;
Cd(II): from approximately 3000 to approximately 3500 ppm, in particular approximately 3200 ppm;
Pb(II): from approximately 10000 to approximately 12000 ppm, in particular approximately 11600 ppm;
Al(III): from approximately 300 to approximately 600 ppm, in particular approximately 430 ppm;

The zinc- and iron(III)-enriched composition obtained after liquid-liquid extraction with trioctylamine comprises a concentration of zinc comprised from approximately 75000 to approximately 150000 ppm, in particular approximately 105000 ppm, and iron(III) at a concentration comprised from approximately 70000 to approximately 75000 ppm, in particular approximately 72100 ppm and optionally one or more metals chosen from the following at the following concentrations:

Mg(II): from approximately 3000 to approximately 4000 ppm, in particular approximately 3600 ppm;
Ca(II): from approximately 25000 to approximately 35000 ppm, in particular approximately 32500 ppm;
Cd(II): from approximately 500 to approximately 1000 ppm, in particular approximately 725 ppm;
Pb(II): from approximately 3000 to approximately 5000 ppm, in particular approximately 4650 ppm;
Al(III): from approximately 3200 to approximately 3800 ppm, in particular approximately 3500 ppm;

The zinc-enriched composition obtained after selective precipitation with NaF comprises a concentration of zinc comprised from approximately 75000 to approximately 150000 ppm, in particular approximately 105000 ppm, and optionally one or more metals chosen from the following at the following concentrations:

Mg(II): from approximately 12000 to approximately 18000 ppm, in particular approximately 15500 ppm;
Ca(II): from approximately 20000 to approximately 25000 ppm, in particular approximately 22500 ppm;
Fe(III): from approximately 2000 to approximately 2500 ppm, in particular approximately 2150 ppm
Cd(II): from approximately 7000 to approximately 7500 ppm, in particular approximately 7250 ppm;
Pb(II): from approximately 3200 to approximately 3800 ppm, in particular approximately 3600 ppm;
Al(III): from approximately 600 to approximately 900 ppm, in particular approximately 730 ppm;

The zinc- and iron(III)-enriched composition obtained after selective precipitation as a function of the pH, in particular at pH<10 comprises a concentration of zinc comprised from approximately 100000 to approximately 150000 ppm, in particular approximately 127000 ppm, and iron(III) at a concentration comprised from approximately 50000 to approximately 60000 ppm, in particular approximately 53800 ppm, and optionally one or more metals chosen from the following at the following concentrations:

Mg(II): from approximately 20000 to approximately 25000 ppm, in particular approximately 23500 ppm;
Ca(II): from approximately 45000 to approximately 50000 ppm, in particular approximately 47300 ppm;
Cd(II): from approximately 9000 to approximately 12000 ppm, in particular approximately 10200 ppm;
Pb(II): from approximately 25000 to approximately 30000 ppm, in particular approximately 28500 ppm;
Al(III): from approximately 12000 to approximately 15000 ppm, in particular approximately 14100 ppm;

The zinc-enriched composition obtained after liquid/solid extraction by washing with acetone comprises a concentration of zinc comprised from approximately 150000 to approximately 200000 ppm, in particular approximately 186000 ppm, and optionally one or more metals chosen from the following at the following concentrations:

Mg(I): from approximately 12000 to approximately 17000 ppm, in particular approximately 14400 ppm;
Ca(II): from approximately 65000 to approximately 75000 ppm, in particular approximately 70900 ppm;
Fe(III): from approximately 14000 to approximately 18000 ppm, in particular approximately 16000 ppm;
Cd(II): from approximately 8000 to approximately 12000 ppm, in particular approximately 10750 ppm;
Pb(II): from approximately 100 to approximately 300 ppm, in particular approximately 221 ppm;
Al(III): from approximately 250 to approximately 350 ppm, in particular approximately 289 ppm;

In an advantageous embodiment, the invention relates to the use of a calcined plant or calcined plant part having accumulated at least one metal in the M(II) form as defined above, in which the purification of the composition leads to a purified composition and the iron present in the M(III) form is in a proportion of less than 2% by weight with respect to the concentration of zinc or completely eliminated, said purification being carried out according to a method chosen from: liquid-liquid extraction with versatic acid or (2-ethylhexyl)phosphoric acid, or a reduction by sodium sulphite.

The composition comprising less than 2% by weight of Fe(III) with respect to the concentration of zinc, obtained after liquid-liquid extraction with versatic acid comprises a concentration of zinc comprised from approximately 47000 to approximately 50000 ppm, in particular approximately 48800 ppm, and optionally one or more metals chosen from the following at the following concentrations:

Mg(I): from approximately 8000 to approximately 12000 ppm, in particular approximately 14400 ppm;
Ca(II): from approximately 90000 to approximately 110000 ppm, in particular approximately 99700 ppm;
Cd(II): from approximately 2000 to approximately 4000 ppm, in particular approximately 3240 ppm;
Pb(II): from approximately 10000 to approximately 15000 ppm, in particular approximately 12880 ppm;
Al(III): from approximately 450 to approximately 650 ppm, in particular approximately 556 ppm;

The composition comprising less than 2% by weight of Fe(III) with respect to the concentration of zinc, obtained after liquid-liquid extraction with (2-ethylhexyl)phosphoric acid comprises a concentration of zinc comprised from approximately 25000 to approximately 35000 ppm, in particular approximately 31650 ppm, and optionally one or more metals chosen from the following at the following concentrations:

Mg(II): from approximately 8000 to approximately 12000 ppm, in particular approximately 10830 ppm;
Ca(II): from approximately 90000 to approximately 110000 ppm, in particular approximately 103450 ppm;
Cd(II): from approximately 7000 to approximately 9000 ppm, in particular approximately 8810 ppm;
Pb(II): from approximately 700 to approximately 1000 ppm, in particular approximately 890 ppm;
Al(III): from approximately 30 to approximately 50 ppm, in particular approximately 50 ppm;

The composition completely devoid of iron(III), obtained after reduction of iron(III) to iron(II) by sodium sulphite comprises a concentration of zinc comprised from approximately 75000 to approximately 105000 ppm, in particular approximately 89900 ppm, iron(II) at a concentration comprised from approximately 1000 ppm to approximately 1300, in particular 1130 ppm, and optionally one or more metals chosen from the following at the following concentrations:

Mg(II): from approximately 2000 to approximately 4000 ppm, in particular approximately 2760 ppm;
Ca(II): from approximately 50000 to approximately 70000 ppm, in particular approximately 58400 ppm;
Cd(II): from approximately 1500 to approximately 3000 ppm, in particular approximately 2300 ppm;
Pb(II): from approximately 11000 to approximately 14000 ppm, in particular approximately 12900 ppm;
Al(III): from approximately 3500 to approximately 5500 ppm, in particular approximately 4560 ppm;

In an advantageous embodiment, the invention relates to the use of a calcined plant or calcined plant part having accumulated at least one metal in the M(II) form chosen in particular from zinc (Zn), nickel (Ni) or copper (Cu), as defined above, in which the composition is combined with a solid support, in particular of activated carbon, clays in particular montmorillonite, alumina, silica, barite, silicates, aluminosilicates, metal oxide-based composites such as ferrite.

For reasons of reactivity, it can be beneficial to combine said composition with activated carbon which has a large specific surface area giving the catalyst a high absorption capacity and therefore reaction rates greater than those carried out without activated carbon.

For certain reactions, in particular the electrophilic aromatic substitutions, dispersion on a solid support, in particular of montmorillonite or silica impregnated with ferric oxides is necessary to the reaction; otherwise a degradation of the reaction products is observed.

Supports such as silica impregnated with metal oxides, in particular ferric oxides or montmorillonite have a specific surface area ranging from 5 m²/g to 800 m²/g respectively.

According to another aspect, the invention relates to a method for preparing a composition devoid of chlorophyll, as defined above, containing at least one metal catalyst in the M(II) form, the metal of which is chosen in particular from Zn, Ni or Cu, comprising the following steps:

a. calcining of a plant or plant part having accumulated at least one metal in the M(II) form chosen in particular from Zn, Ni or Cu, in order to obtain a calcined plant or calcined plant part, b. stifling of said calcined plant or calcined plant part in an acid, in particular hydrochloric acid or sulphuric acid, in order to destructure the calcined plant or plant part and in order to obtain a mixture containing the calcined and destructured plant or plant part and at least one metal catalyst the metal of which is chosen in particular from Zn, Ni or Cu, c. concentration of aforesaid mixture containing the calcined plant or calcined and destructured plant part and at least one metal catalyst in order to obtain a concentrated mixture containing a calcined and destructured plant or plant part and at least one metal catalyst chosen in particular from Zn, Ni or Cu in a proportion greater than that obtained in b., d. filtration of aforesaid concentrated mixture in order to obtain a filtrate and a precipitate, said filtrate corresponding to a crude composition devoid of chlorophyll containing at least one metal catalyst the metal of which in the M(II) form is chosen in particular from Zn, Ni or Cu, and the pH of said filtrate being adjusted as a function of the metal, under conditions such that the pH of the composition is ≤5 for Zn, approximately equal to 7 for Ni and comprised between 2 and 7 for Cu.

The first calcining step a. is carried out by heating at a high temperature and makes it possible to remove the water present and largely destroy the biomass.

It can also be carried out by dehydration by heating the plant or plant parts, i.e. the biomass, then grinding the dehydrated biomass.

This step is decisive for obtaining the catalyst as it leads to the more or less significant destruction of the vegetable matter in order to facilitate its subsequent complete degradation in acid medium.

Calcining makes it possible to obtain a greater final proportion of catalyst than dehydration.

The acid treatment of the second step b. makes it possible to destructure the plant or plant parts, i.e. to destroy certain biological membranes, in particular those of the vacuoles in order to release the metal carboxylates, in particular the zinc and/or nickel and/or copper, and/or other metal carboxylates, in order form a metal chloride in the case of the use of HCl or a metal sulphate in the case of the use of sulphuric acid.

The treatment also allows the complete hydrolysis of the ester bond between the fatty chain and the pyrrole ring of the chlorophyll.

In the standard methods, the chlorophyll is removed by extraction with hexane. When this method is used in the invention instead of the acid treatment, the metal remains in the vacuoles of the vegetable matter and it cannot be recovered in order to obtain the catalyst.

The reaction medium therefore contains a mixture of metal chlorides or sulphates as well as other compounds resulting from the degradation of the biomass after dehydration or calcining and acid treatment as well as cellulose and chlorophyll degradation products in particular:

The concentration carried out in step c. makes it possible to increase the concentration of metal catalyst in the medium as well as the acid concentration in order to obtain optimum effectiveness of the catalyst during the implementation of the organic reaction. The pH must then be acid in order to prevent the formation and precipitation of the metal hydroxides.

The last step d. is also essential for the utilization of the catalyst.

In fact, it makes it possible to completely remove the chlorophyll residues which remain on the filtration system, in particular a frit, which leads to a colourless filtrate containing the metal catalyst, which therefore no longer contains chlorophyll or chlorophyll residues, being obtained.

If step d. is carried out by centrifugation or by lyophilization, therefore without filtration, the subsequent implementation of the organic reaction is not possible as the chlorophyll or the chlorophyll residues strongly prevent the reaction and lead to a strongly coloured medium.

Thus Example 12 shows that the reaction on a secondary alcohol carried out with a composition containing a zinc catalyst, obtained without filtration, does not lead to the desired halogenated derivative (only traces after reaction for 5 hours), unlike the composition of Example 3, obtained with filtration, which leads to the halogenated derivative with a yield of 40% after reacting for 3 hours. The filtration makes it possible to obtain organic reactions with a yield at least equal to 18% by treating with 1N HCl and dehydration, in particular 47 to 94% by treating with 12N HCl and calcining.

In an advantageous embodiment, the method defined above makes it possible to obtain organic reactions with a yield at least greater than 18%.

In an advantageous embodiment, the method defined above makes it possible to obtain organic reactions, except in the case of the primary alcohol: hexanol-1, with a yield at least greater than 35%.

The pH must be controlled after filtration at a value which is a function of the metal used in order to produce a composition having for example a pH≤5 for Zn, approximately equal to 7 for Ni and comprised between 2 and 7 for Cu so that the organic reaction can be subsequently implemented. In fact, the metal catalyst at this pH remains in solution and does not precipitate.

In the case where the pH is greater than 5 in the case of zinc or for metals requiring an acid pH, it must be corrected to a value of less than or equal to 2 by the addition of acid, in particular of dilute or concentrated HCl, i.e. 0.1N, or 1N to 12N HCl, or also of gaseous HCl by bubbling through.

The composition obtained therefore contains at least one metal catalyst as well as compounds resulting from the degradation of the vegetable raw material such as complete or partial cellulose degradation products, such as cellobiose which originates from the depolymerization of cellulose and which can itself be completely or partially degraded to glucose which can be itself be completely or partially degraded to products such as 5-hydroxymethylfurfural or formic acid.

In an advantageous embodiment, the invention relates to a method for preparing a composition as defined above, in which:

step a. is carried out at a temperature comprised from approximately 200° C. to approximately 800° C., in particular 300° C. over approximately 1 hour to 3 hours, in particular 2 hours, then cooling down to 25° C., step b. is carried out with gaseous hydrochloric acid, dilute or concentrated aqueous hydrochloric acid, in particular concentrated, over approximately 30 minutes to approximately 2 hours, in particular 1 hour, step c. is carried out:
by partial evaporation or,
by sonication over approximately 1 to approximately 3 hours and the addition of dilute or concentrated hydrochloric acid.

The calcining of step a. must be carried out at a temperature high enough for calcining, i.e. in order to obtain complete combustion of the biomass but not too high as the process becomes difficult to use in an industrial environment.

Below 200° C., the temperature does not allow complete combustion.

Above 800° C., the temperature is too high to be easily used in an industrial environment.

The acid used is preferably gaseous or aqueous hydrochloric acid, and can be dilute or concentrated, i.e. 0.1N, or 1N to 12N HCl. However the best results for the subsequent implementation of the organic reaction are obtained with concentrated HCl, i.e. 12N.

Sonication makes it possible to destroy more of the chlorophyll and causes heating which leads to concentration of the medium. It is however necessary to add concentrated (12N) hydrochloric acid in order to control the pH.

Sonication therefore leads to a metal catalyst being obtained with a greater yield than in case of the method without sonication.

Below 1 hour, the heating caused is not enough to concentrate sufficiently; beyond three hours the concentration becomes too high.

In the case where sonication is not carried out, a partial evaporation is necessary to increase the acid concentration.

The composition therefore contains at least one metal catalyst such as zinc dichloride and/or nickel dichloride and/or cupric chloride in a majority proportion and/or a metal chloride constituted by other metals such as lead, cadmium, arsenic, cobalt, chromium, manganese or thallium as a function of the proportion of metals present in the plant before calcining, as well as the compounds resulting from degradation of the vegetable raw material after the different steps of the method.

In an advantageous embodiment, the composition obtained by the above method after acid treatment is devoid of activated carbon.

In an advantageous embodiment, the composition obtained by the above method after acid treatment comprises less than approximately 2%, in particular less than approximately 0.2% by weight of C, in particular approximately 0.14%.

In an advantageous embodiment, the invention relates to a method for preparing a composition as defined above, in which said plant belongs to the Brassicaceae family, in particular *Thlaspi caerulescens* or *Arabidopsis hallerii*, said acid is 1N HCl and the metal of said composition is Zn and optionally comprises at least one metal chosen from Mg, Ca, Fe(III), Al(III), Cu, Cd, Pb, Na, Mn, Ni.

In an advantageous embodiment, the invention relates to a method for preparing a composition as defined above, in which said plant belongs to the Brassicaceae family, in particular *Thlaspi caerulescens* or *Arabidopsis hallerii*, said acid is 12N HCl and the metal of said composition is Zn, and said composition comprises optionally at least one metal chosen from: Mg, Ca, Fe(III), Al(III), Cu, Cd, Pb.

In an advantageous embodiment, the zinc in the composition is at a concentration comprised from approximately 15000 to approximately 800000 ppm, in particular from approximately 20000 to approximately 80000 ppm, in particular from approximately 61 000 to approximately 67700 ppm, said composition also comprising one or more metals from the following list at the following concentrations:

Mg(II): from approximately 2500 to approximately 25000 ppm, in particular from approximately 4400 to approximately 15000 ppm, in particular from approximately 11800 to approximately 13100 ppm;

Ca(II): from approximately 20000 to approximately 100000 ppm, in particular from approximately 73000 to approximately 91000 ppm;

Fe(III): from approximately 900 to approximately 75000 ppm, in particular from approximately 3100 to approximately 30000 ppm, in particular from approximately 8700 to approximately 28000 ppm;

Cu(II): from approximately 30 to approximately 400 ppm, in particular from approximately 55 to approximately 170 ppm, in particular from approximately 99 to approximately 170 ppm;

Cd(II): from approximately 700 to approximately 10000 ppm, in particular from approximately 1800 to approximately 5600 ppm, in particular from approximately 5300 to approximately 5600 ppm;

Pb(II): from approximately 200 to approximately 40000 ppm, in particular from approximately 4600 to approximately 15000 ppm, in particular from approximately 13000 to approximately 15000 ppm;

Al(III): from approximately 200 to approximately 15000 ppm, in particular from approximately 2400 to approximately 6000 ppm, in particular from approximately 1500 to approximately 4700 ppm.

In an advantageous embodiment, the invention relates to a method for preparing a composition as defined above, also comprising a step of purification of said composition, according to a method chosen from: an ion exchange resin, liquid-liquid extraction with trioctylamine, selective precipitation, in particular with NaF or as a function of the pH, liquid/solid extraction by washing with acetone, in order to obtain a purified composition enriched with Zn and/or Fe(III).

In an advantageous embodiment, the invention relates to a method for preparing a composition as defined above, also comprising a step of purification according to a method chosen from: liquid-liquid extraction with versatic acid or (2-ethylhexyl)phosphoric acid, or reduction with sodium sulphite in order to obtain a purified composition comprising less than 2% by weight of iron(III) with respect to the concentration of zinc or completely devoid of iron(III).

In an advantageous embodiment, the invention relates to a method for preparing a composition as defined above, in which said plant is a Sapotaceae, in particular *Sebertia acuminata*, a Rubiaceae, in particular *Psychotria douarrei*, or a Brassicaceae, in particular *Thlaspi goesingense* or *Thlaspi caerulescens*, said acid is 12N HCl and the metal in said composition is Ni, and said composition optionally comprises at least one metal chosen from: Mg, Al(III), Ca, Fe(III), Cu, Zn, Cd, Pb, Mn.

In an advantageous embodiment, the invention relates to a method for preparing a composition as defined above, in which said plant is a Convolvulaceae, in particular *Ipomea alpina* or a Brassicaceae, in particular *Thlaspi caerulescens*, or a Scrophulariaceae, in particular *Bacopa monnieri*, said acid is 12N HCl and the metal in said composition is Cu, and said composition optionally comprises at least one metal chosen from: Mg, Al(III), Ca, Fe(III), Zn, Cd, Pb, Ni.

In an advantageous embodiment, the invention relates to a method for preparing a composition as defined above, in which the water in the composition obtained in step d. is completely evaporated in order to obtain a dehydrated composition containing said catalyst.

In order to implement certain organic reactions, a catalyst containing very little or no water is required.

Consequently, evaporation makes it possible to obtain a dehydrated medium where only the highly hygroscopic catalyst can remain combined with a limited number of water molecules.

According to another aspect, the present invention relates to a method for implementing an organic synthesis reaction comprising a step of bringing a composition devoid of chlorophyll containing at least one metal catalyst the metal of which in the M(II) form is chosen in particular from Zn, Ni or Cu, as defined above, into contact with at least one chemical compound capable of reacting with said composition.

One of the advantages of the invention is the ability to directly use the composition containing the catalyst obtained above, in aqueous acid form or in dehydrated form without subsequent purification and to bring it together with one or more chemical reagents in order to carry out a chemical reaction.

According to another aspect, the present invention relates to a method for implementing an organic synthesis reaction, as defined above, in which said organic synthesis reaction is chosen from halogenations in particular of alcohols, electrophilic aromatic reactions in series, in particular substitutions or additions, catalyst synthesis reactions for coupling or hydrogenation reactions after reduction of Ni(II) to Ni$^0$, synthesis of 3,4-dihydropyrimidin-2(1H)-one or of 3,4-dihydropyrimidin-2(1H)-thione, cycloaddition reactions, and synthesis of amino acid or oxime developers, said composition being optionally purified.

In an advantageous embodiment, the present invention relates to a method for implementing a halogenation reaction in particular of alcohol, as defined above, comprising the following steps:
  a. bringing an alcohol into contact with a composition containing said metal catalyst, optionally purified, the metal of which in the M(II) form is Zn and having a pH less than or equal to 5, as defined above, in order to form an alcohol-catalyst complex.
  b. stirring said complex at ambient temperature or at a temperature comprised from approximately 20 to 60° C., preferably from approximately 20 to 50° C., in particular of approximately 40° C. over approximately 1 to approximately 24 hours, preferably approximately 1 to approximately 12 hours, more preferably from approximately 1 to approximately 6 hours, in particular approximately 3 hours in order to obtain a reaction mixture containing said halogenated derivative,
  c. extraction of said reaction mixture with an organic solvent, in particular petroleum ether, in order to recover said halogenated derivative.

By "alcohol-catalyst" complex, is meant for example the formation of a Lewis acid-base type complex between the alcohol and ZnCl$_2$:

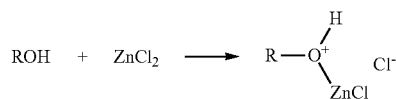

Said complex is then attacked by the chloride ion which by Sn2-type nucleophilic substitution leads to the halogenated derivative by more or less severe heating for a more or less significant period of time as a function of the reactivity of the alcohol:

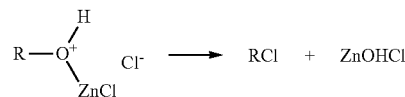

The catalyst is then regenerated by the acid medium in order to re-form ZnCl$_2$:

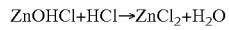

ZnOHCl+HCl→ZnCl$_2$+H$_2$O

The alcohol used can be a primary, secondary or tertiary alcohol and Example 3 presents several alcohols on which the reaction has been carried out.

Example 4 presents a model of a halogenation reaction carried out in a metallophyte species.

Zinc malate was prepared from commercial malic acid and brought into contact with HCl to form the ZnCl$_2$ catalyst which was reacted with 4-methyl-pentan-2-ol which acts as a solvent and a reagent.

The alcohol is then halogenated (chlorination) in the same way as with a metal originating from a plant which accumulates zinc.

In an advantageous embodiment, the present invention relates to a method for implementing a halogenation reaction in particular of alcohols, as defined above, in which the catalyst/alcohol molar ratio of step a. is comprised from approximately 0.01 to approximately 5, preferably from approximately 0.1 to approximately 5, more preferably from approximately 1 to approximately 4, in particular from approximately 2 to 4.

The molar ratio between the catalyst and the alcohol is a function of the alcohol used.

One of the advantages of the invention is the ability to use the catalyst in a catalytic quantity, i.e. significantly less than the stoichiometric quantity required by the alcohol, in a proportion for example of 0.01% with respect to the alcohol.

Below this limit, the reaction is too slow to be capable of being carried out.

However, the reaction is more rapid with a proportion greater than the stoichiometric proportion and the catalyst values advantageously used (in moles) are between 2 and 4 times the number of moles of alcohol.

Beyond 5, the cost of the proportion of catalyst becomes prohibitive.

In an advantageous embodiment, the present invention relates to a method for implementing an organic synthesis reaction, as defined above, in which said organic synthesis reaction is an electrophilic aromatic substitution reaction in series involving two reagents A and B.

Another advantage of the invention is the ability to carry out organic synthesis reactions other than the halogenation of alcohols, and in particular electrophilic substitution reactions such as for example Friedel-Crafts reactions such as the reaction of Example 11.

In an advantageous embodiment, the present invention relates to a method for implementing an organic synthesis reaction, in particular an electrophilic substitution reaction, as defined above, comprising the following steps:
  a. bringing reagents A and B into contact with a dehydrated composition as defined above, and containing said metal catalyst, dispersed on a solid support, the metal of which is Zn, nickel or aluminium, in toluene in order to obtain a reagents A, B-catalyst complex, b. stirring said reagents A, B-catalyst complex at ambient temperature or at a temperature comprised from approximately 10 to 80° C., preferably from approximately 15 to 40° C., in particular from approximately 20° C. over approximately 15 minutes to approximately 15 hours, preferably approximately 5 minutes to approximately 2 hours, in particular approximately 1 hour, in order to obtain an electrophilic substitution product, c. filtration and evaporation in order to recover said substitution product.

If the catalyst is not dispersed on a solid mineral support, the reaction essentially leads to degradation products.

The toluene of step a. acts equally well as a solvent and as a reagent.

In the same manner as for the halogenation of alcohols, a complex is formed between the reagents and the catalyst. Said complex is however not the same as that obtained for the alcohols.

The reaction takes place more or less rapidly and requires more or less heating as a function of the reagents used. Below 10° C., the reaction does not take place. Beyond 80° C., there is a risk of degradation of the reagents.

In an advantageous embodiment, the present invention relates to a method for implementing an organic synthesis reaction, in particular an electrophilic substitution reaction, as defined above, in which the catalyst/A molar ratio of step a. is comprised from approximately 0.01 to approximately 5, preferably from approximately 0.1 to approximately 2, more preferably from approximately 1 to approximately 4, in particular from approximately 2 to 4, and the catalyst/B molar ratio of step a. is comprised from approximately 0.01 to approximately 5, preferably from approximately 0.1 to approximately 5, more preferably from approximately 1 to approximately 4, in particular approximately 2.

One of the advantages of the invention is the ability to use the catalyst in a catalytic quantity, i.e. significantly less than the stoichiometric quantity required with respect to the electrophile (benzyl chloride in the example), in a proportion for example of 0.01% with respect to reagents A and B. Below this limit, the reaction is too slow to be capable of being carried out.

However, the reaction is more rapid with a greater proportion such as 0.1% of catalyst.

A second advantage is the possibility of dispersing the catalyst on a solid mineral support facilitating the operations of separation of the products and the catalyst, then recycling the catalyst.

In an advantageous embodiment, the present invention relates to a method for implementing an organic synthesis reaction, as defined above, in which said organic synthesis reaction is a electrophilic addition reaction involving two reagents C and D.

In an advantageous embodiment, the present invention relates to a method for implementing an organic synthesis reaction, in particular an electrophilic addition reaction as defined above, comprising the following steps:
a. bringing reagents C and D of the reaction into contact with an anhydrous composition as defined above, in order to obtain a reagents C, D-catalyst complex
b. stifling said C, D-catalyst complex at ambient temperature or at a temperature comprised from approximately 20 to 100° C., in order to obtain an electrophilic addition product,
c. extraction with an organic solvent, in order to recover said electrophilic addition product.

The solvents that can be used for the extraction are well known to a person skilled in the art.

In an advantageous embodiment, the present invention relates to a method for implementing an organic synthesis reaction, as defined above, in which the catalyst/C molar ratio is comprised from approximately 0.01 to approximately 5, preferably from approximately 0.1 to approximately 5, more preferably from approximately 1 to approximately 4, in particular from approximately 2 to 4, the catalyst/D molar ratio being comprised from approximately 0.01 to approximately 5, preferably from approximately 0.1 to approximately 5, more preferably from approximately 1 to approximately 4, in particular from approximately 2 to 4.

One of the advantages of the invention is the ability to use the catalyst in a catalytic quantity, i.e. significantly less than the stoichiometric quantity required by the alcohol, in a proportion for example of 0.01% with respect to reagents C and D.

Below this limit, the reaction is too slow to be capable of being carried out.

However, the reaction is more rapid with a proportion greater than the stoichiometric proportion and the catalyst values advantageously used (in moles) are between 2 and 4 times the number of moles of reagent.

Beyond 5, the cost of the proportion of catalyst becomes prohibitive.

In an advantageous embodiment, the present invention relates to a method for implementing an organic synthesis reaction, in which said organic synthesis reaction is a synthesis reaction of 3,4-dihydropyrimidin-2(1H)-one (or thione).

In an advantageous embodiment, said synthesis reaction of 3,4-dihydropyrimidin-2(1H)-one (or thione) comprises the following steps:
a. bringing an aromatic aldehyde, urea or thiourea and an alkyl acetoacetate into contact with a purified composition enriched with zinc or containing dehydrated nickel, as defined above, mixed beforehand with a solid mineral support such as silica, in toluene in order to obtain an aromatic aldehyde-urea or a thiourea-catalyst complex,
b. stifling said aromatic aldehyde-urea or a thiourea-catalyst complex at a temperature comprised from approximately 80 to 120° C., in particular from approximately 110° C. for approximately 1 h min to approximately 24 hours, preferably approximately 5 minutes to approximately 15 hours, in particular approximately 10 hours, in order to obtain a 3,4-dihydropyrimidin-2(1H)-one (or thione),
c. filtration and evaporation in order to recover said 3,4-dihydropyrimidin-2(1H)-one (or thione).

In an advantageous embodiment, the present invention relates to a method for implementing an organic synthesis reaction, in which said organic synthesis reaction is a cycloaddition reaction.

In an advantageous embodiment, said cycloaddition reaction comprises the following steps:
a. bringing an alkene in solution in a solvent such as toluene into contact with a composition enriched with zinc and iron and dehydrated, or containing nickel or aluminium, as defined above, in solution in a solvent such as toluene, and stirring the reaction medium for approximately 1 minute to 1 hour, in particular 30 minutes at ambient temperature, in order to obtain a dienophile-catalyst complex,
b. addition of a diene and stifling for approximately 5 minutes to 2 hours, in particular 15 minutes at a temperature comprised between −70° C. and 25° C. in order to obtain a cycloaddition product,
c. hydrolysis, liquid-liquid extraction and evaporation in order to recover said cycloaddition product.

In an advantageous embodiment, the present invention relates to a method for implementing an organic synthesis reaction, in which said organic synthesis reaction is a catalyzed hydrolysis reaction of the sulphur-containing organic functions, in particular the thiophosphates.

In an advantageous embodiment, said catalyzed hydrolysis reaction of the sulphur-containing organic functions comprises the following steps:
a. bringing a sulphur-containing compound to be hydrolyzed into contact with a composition enriched with copper or zinc and dehydrated, as defined above, in solution in a mixture of solvent such as water and ethanol, and stirring the reaction medium for approximately 24 to 48 h, in particular 30 h at a temperature comprised from 20 to 80° C., in particular 40° C., in order to obtain a hydrolyzed sulphur-containing compound,
b. washing in a basic medium, in particular with soda and evaporation in order to recover said hydrolyzed compound.

According to another aspect, the present invention relates to a composition devoid of chlorophyll containing at least one metal catalyst the metal of which is chosen in particular from Zn, Ni or Cu as defined above, comprising at least one of said metals in the form of chloride or sulphate, and cellulose degradation fragments such as cellobiose and/or glucose, and/or glucose degradation products such as 5-hydroxymethylfurfural and formic acid and less than approximately 2%, in particular less than approximately 0.2% by weight of C, in particular approximately 0.14%.

The composition therefore corresponds to one or more metal chlorides depending on the plant, the soil on which it has grown and as a result, the metals that it has been able to absorb, in the case where hydrochloric acid was used for the method of preparation of said composition.

It comprises one or more metal sulphates in the case where sulphuric acid was used.

Whatever the composition (chloride or sulphate), it also comprises cellulose degradation products described above which however does not prevent a satisfactory outcome.

In an advantageous embodiment, the present invention relates to a composition containing at least one metal catalyst the metal of which is chosen in particular from Zn, Ni or Cu as defined above, in an acidified solution, in particular aqueous hydrochloric or sulphuric acid.

In this embodiment, the composition obtained after the filtration defined above is obtained in solution in an acid, in particular aqueous hydrochloric or sulphuric acid and can be used as it is, without subsequent purification or treatment for utilization in organic reactions.

In an advantageous embodiment, the present invention relates to a composition containing at least one metal catalyst the metal of which is chosen in particular from Zn, Ni or Cu as defined above, devoid of activated carbon.

In an advantageous embodiment, the present invention relates to a composition containing at least one metal catalyst the metal of which is chosen in particular from Zn, Ni or Cu as defined above, in dehydrated form.

For certain organic reactions to be implemented, it is necessary to have the catalyst available without the presence of water and as a result, the composition must be dehydrated after it has been obtained by the method of the invention or by another method, before use, by evaporation or by heating so as to obtain a composition containing very little or no water, where only the highly hygroscopic catalyst can remain combined with a limited number of water molecules.

The preparation of a catalyst in an acid medium facilitates its subsequent dehydration: thus $NiCl_2$ is obtained without being combined with water molecules after being simply placed in an oven: the yellow colour shows its total dehydration.

According to another aspect, the present invention relates to a composition as obtained by implementation of the method as defined above.

EXAMPLES

Example 1

Figure 1:
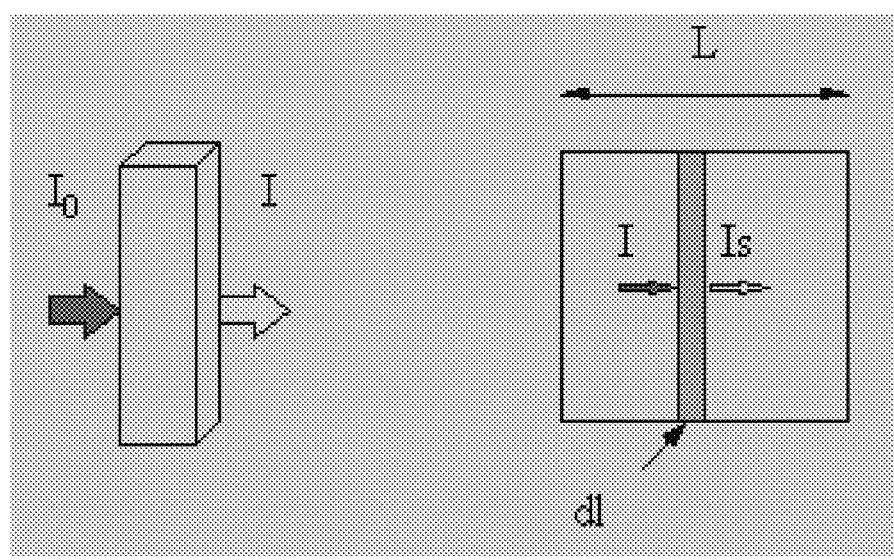
FIG. 1 illustrates the general principles of spectrometry, in which light absorption is demonstrated by the number of photons (light intensity) that is lower when leaving the sample than when entering.

Preparation of a Composition Containing a Metal Catalyst the Metal of which is Zn 1.1: Obtaining the Crude Catalyst 30.03 g dehydrated and powdered leaves of *Thlaspi caerulescens* originating from the soil of the mine at Avnières are assayed by Escarré's method (zincon assay) in order to measure the level of zinc present in the dry matter (in the used and calcined samples: 420 mg or 2 mmoles: average level, depending on the site where the leaves are collected). The dry matter is then placed in 20 mL of 1N hydrochloric acid.

Note: Dehydration is either calcining (approximately 300° C. for 2 hours: ash is then obtained), or heating at 100° C. under vacuum for 4 to 5 hours followed by grinding with a mortar). The mass of dry matter is then different (more organic products degraded and lost by calcining, see Table II below).

TABLE II

| | Results in ppm (ICP-MS) | | | | | | | |
|---|---|---|---|---|---|---|---|---|
| | Mg | Al | Ca | Fe | Cu | Zn | Cd | Pb |
| dehydration | 4394 | 2468 | 73827 | 3095 | 57 | 22501 | 1863 | 4653 |
| calcining | 11816 | 4726 | 90860 | 8738 | 99 | 61040 | 5498 | 12992 |

The above values are those obtained after treatment with 1N HCl and filtration.

The metals present in Table II are in the M(II) form except for the iron which is in the M(III) form.

An alternative consists of treating the dry matter with 20 ml of 12N HCl.

A fine and detailed analysis of the composition of the media was carried out by ICP-MS, the method using zincon (for the zinc) and pulse polarography.

The results are all consistent and are repeated 3 times (expressed in ppm);

Cl was assayed by the Mohr method (formation of the red $Ag_2CrO_4$ complex).

C and N were assayed by the CHN dry method. The average values are summarized in Table III below:

TABLE III

| | Catalyst | | | | | | | | | | | | | | | |
|---|---|---|---|---|---|---|---|---|---|---|---|---|---|---|---|---|
| | Mg ppm | Ca ppm | Fe ppm | Cu ppm | Zn ppm | Cd ppm | Pb ppm | Na ppm | K ppm | P ppm | Mn ppm | Ni ppm | Co ppm | Cl ppm | C % | N % |
| With 1N HCl | 11816 | 90860 | 8738 | 99 | 61040 | 5498 | 12992 | 23000 | 28000 | 9500 | 360 | 25 | — | ND | ND | ND |
| With 12N HCl | 13182 | 73827 | 27859 | 170 | 67744 | 5589 | 14946 | — | — | — | — | — | — | 3441 | 0.14 | 0.021 |

ND: Not determined

The treatment with 12N HCl changes the composition, in particular enriches it with zinc(II) and iron (III) and relatively reduces the proportion of Ca.

The solution is stirred for 1 hour, then sonicated for 2 hours. The medium is concentrated by heating the reaction medium. 1 to 2 mL of 12N HCl are added in order to allow satisfactory stifling of the medium.

Note: if sonication is not required, concentration of the reaction medium must be provided, followed by the addition of 12N HCl.

The solution is filtered on a frit having a porosity of 4. The solid residue is washed with 2 mL of 12N HCl. The filtrate must be perfectly clear. The pH is checked and optionally adjusted to a value less than 2 if necessary by the addition of 12N HCl. Rapid measurement of the zinc in solution by atomic absorption spectroscopy (Spectra Varian AA 220FS spectrometer) (*Thlaspi caerulescens, un indicateur de la pollution d'un sol ? Une réflexion partagée entre étudiants et chercheurs autour d'un problème environnemental* C. GRISON, J. ESCARRE, M. L. BERTHOMME, J. COUHET-GUICHOT, C. GRISON, F. HOSY, Actualité Chimique, 2010, 340, 27-32) makes it possible to check the recovered level of zinc (in the form of $ZnCl_2$). Under the conditions described, on average 70% of the zinc initially introduced is recovered, in this case 1.4 mmoles.

1.2: Purification of the Catalyst Obtained in Example 1.1 with 12N HCl 1.2.1: Enrichment with $Zn^{2+}$ and $Fe^{3+}$ Amberlyte IRA400 Resin (or Dowex 1)

Before use, the resin must be left to swell for 24 hours in a 9N HCl solution. In order to separate 500 mg of product, 30 g of resin will be used. After swelling, the resin can be introduced into a column (9M HCl will be used in order to entrain the resin) at the ends of which cotton will be placed and, at the bottom, Fontainebleau sand on the cotton.

The catalytic solution is then passed over the resin. Then the resin is rinsed for a first time with 150 mL of a 0.5N HCl solution at a rate of 3 mL per minute. The standard step of recovery of the zinc bound to the resin by passing a 0.005N HCl solution over it is not sufficient. The resin must be extracted from the column, then placed in a beaker containing 100 mL of a 0.005N HCl solution. The whole is placed under magnetic stirring and heated for 1 day at 50° C.

In order to handle larger quantities of resin, better control the contact time and not have to prepare the column only to dismantle it before the re-extraction step, a crystallizer of a suitable size was used under magnetic stirring.

The resin is left in contact with the catalytic solution under magnetic stirring for 10 minutes. This is sufficient to extract 95% of the zinc present in the catalytic solution: the latter is found bound to the resin complexed by chloride ions.

The step of rinsing with 0.5M HCl which is intended to elute the iron is carried out under the same conditions: 10 minutes under magnetic stirring. The volume of the rinsing solution is adapted to the quantity of resin in order to recover it. Additional rinsing with 0.005M HCl makes it possible to remove the last traces of iron.

results: complete mass balance at each step and mass of each element remaining on the resin (Table IV):

TABLE IV

| | Mass obtained in mg | | | | | | |
|---|---|---|---|---|---|---|---|
| | Mg | Al | Ca | Fe | Zn | Cd | Pb |
| Cat. Sol 12M HCl | 83.58 | 57.25 | 528.36 | 253.69 | 385.57 | 23.49 | 106.68 |
| After Passing over Resin | 64.27 | 43.57 | 363.54 | 66.00 | 10.07 | 0.74 | 14.55 |
| Rinsing the resin with 0.5M HCl | 10.87 | 5.58 | 68.94 | 67.35 | 2.05 | 0.09 | 5.83 |
| Rinsing the resin with 0.005M HCl | 5.56 | 2.60 | 34.31 | 63.41 | 23.80 | 0.20 | 15.85 |
| Remaining on the resin | 2.87 | 5.49 | 61.57 | 56.90 | 349.64 | 22.44 | 70.43 |
| Yield % | 3.4 | 9.5 | 11.6 | 22.4 | 90.6 | 95.5 | 66.0 |

Thorough washing with water (the resin is left in water for 12 hours under magnetic stirring) and filtration under vacuum make it possible to recover most of the zinc present initially (final mass: 319 mg, i.e. 83% yield). The analysis of the recovered residue is as follows:

| | Results in ppm (ICP-MS) | | | | | | |
|---|---|---|---|---|---|---|---|
| | Mg | Al | Ca | Fe | Zn | Cd | Pb |
| After washing with water | 13973 | 430 | 20250 | 2610 | 704330 | 3170 | 11540 |

The technique is simple and very effective; the solid obtained is kept in an oven at 90° C. and used in organic synthesis.

Liquid-Liquid Extraction with Trioctylamine (TOA)

A scale model of an industrial reactor was used for this method, making it possible to introduce and recover the different phases without having to dismantle the device. The organic phase which allows the extraction of the zinc is a 5% solution by mass of trioctylamine in toluene.

For a catalytic solution prepared from 1 g of ash, we therefore used 1.7 g (2.1 mL) of trioctylamine in solution in 32.3 g (37.1 mL) of toluene.

The catalytic solution obtained from 1 g of ash is brought into contact with the solution of trioctylamine in toluene. The whole is left for 12 hours under mechanical stirring in our reactor.

The organic phase is then recovered and cleaned with 2N HCl for 2 minutes. This step is carried out in a separating funnel and with manual stifling.

The cleaned organic phase is then returned to the reactor then 10 mL of a 0.05N HCl solution is added. It is left under mechanical stirring for half a day. The aqueous phase is recovered, then the process is repeated with 10 mL of 0.05N HCl solution. The two aqueous phases are combined, finally obtaining 20 mL of 0.05N HCl solution from which the zinc should have been recovered.

results (Table V):

TABLE V

| TOA extract | ICP-MS UM2 | | | | | | |
|---|---|---|---|---|---|---|---|
| | Mg ppm | Al ppm | Ca ppm | Fe ppm | Zn ppm | Cd ppm | Pb ppm |
| cg0 catalytic solution | 11816 | 4726 | 90860 | 8738 | 61040 | 5498 | 12992 |
| cg1 aq. ph. after extr. | 18670 | 7252 | 121300 | 274 | 27380 | 1633 | 20540 |
| cg2 aq. ph. after 2M HCl | 2724 | 1171 | 18058 | 2492 | 22880 | 972 | 4930 |
| cg3 aq. ph. after 0.05M HCl | 3520 | 3454 | 32020 | 72080 | 103320 | 723 | 4650 |
| concentration factor % | 30 | 73 | 35 | 824 | 169 | 13 | 35 |

Selective Precipitations with NaF

The catalytic solution is adjusted to pH=4 by the progressive addition of soda. Excess sodium fluoride is added. $MgF_2$ et $CaF_2$ precipitate. After centrifugation, the supernatant is adjusted to pH=10 by adding aqueous soda. The precipitate is centrifuged then analyzed. It is highly enriched with Zn(II). Treatment with concentrated HCl makes it possible to regenerate a catalytic solution enriched with $ZnCl_2$.

results (Table VI):

TABLE VI

Figure 3:
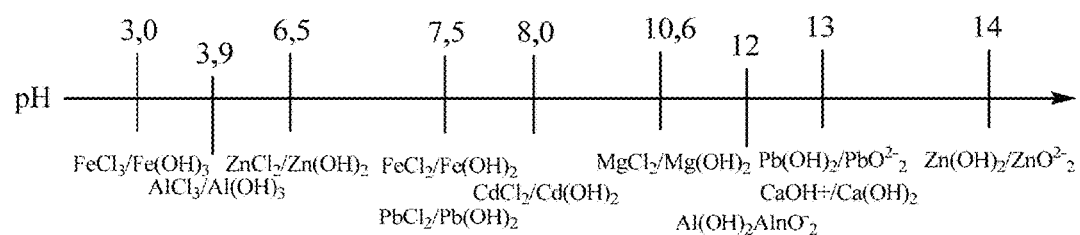
FIG. 3 illustrates the selective precipitation of catalytic compounds as a function of pH.

| | ICP-MS UM2 | | | | | | |
|---|---|---|---|---|---|---|---|
| | Mg ppm | Al ppm | Ca ppm | Fe ppm | Zn ppm | Cd ppm | Pb ppm |
| catalytic solution | 16083 | 6323 | 102795 | 14943 | 72095 | 6116 | 19775 |
| supernatant after centri. | 3590 | 152 | 21050 | 416 | 19741 | 1672 | 806 |
| precipitate pH > 10 | 15497 | 723 | 22380 | 2119 | 80113 | 7240 | 3580 |
| supernatant at pH 10.8 | 199 | 62 | 18297 | 144 | 302 | 29 | 38 |
| concentration factor % | 96 | 11 | 21 | 14 | 111 | 118 | 18 | selective precipitations as a function of the pH by the addition of NaOH 1M principle: to precipitate the different species with the pH
See FIG. 3
results (Table VII):

TABLE VII

| | Mg | Al | Ca | Fe | Zn | Cd | Pb |
|---|---|---|---|---|---|---|---|
| catalyst | 13182 | 7404 | 73827 | 27859 | 67744 | 5589 | 14946 |
| Precipitate pH < 10 | 23467 | 14096 | 47298 | 53784 | 126524 | 10114 | 28483 |

TABLE VII-continued

| | Mg | Al | Ca | Fe | Zn | Cd | Pb |
|---|---|---|---|---|---|---|---|
| supernatant | 2518 | 990 | 52193 | 1071 | 529 | 59 | 392 |
| Concentrate Factor % | 178 | 190 | 64 | 193 | 186 | 180 | 190.57 |

The $Fe^{3+}$ and $Zn^{2+}$ coprecipitate: only the calcium shows a reduction in concentration while the concentrations of the other species increase.

At pH 10, most of the zinc is in the form of $Zn(OH)_2$ and is found in the recovered precipitate. Improving the selectivity of the process can be envisaged by stopping at a lower pH: the concentration factor of the magnesium reduces and that of the zinc increases while the zinc yield drops.

1.2.2: Removal of the $Fe^{3+}$

The removal of $Fe^{3+}$ is not imperative, but it can offer 2 advantages:

a/ allowing clear precipitation of $Zn(OH)_2$. ($Fe(OH)_3$ precipitates from pH 3 in colloidal form and entrains a portion of $Zn^{2+}$).

b/ facilitating AAS analyses (the precipitation of $Fe(OH)_3$ from pH=3 poses technical problems of concern to analysts) reducing the Fe3+ in the crude catalyst with sodium sulphite Principle: Reducing the $Fe^{3+}$ to $Fe^{2+}$ with $SO_2$

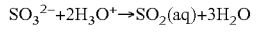

$$SO_3^{2-}+2H_3O^+ \rightarrow SO_2(aq)+3H_2O$$

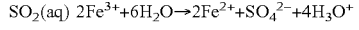

$$SO_2(aq)\ 2Fe^{3+}+6H_2O \rightarrow 2Fe^{2+}+SO_4^{2-}+4H_3O^+$$

Protocol: 1 mL of 1M HCl is added to a 0.1M $Na_2SO_3$ solution in a 5 mL beaker. Sulphur dioxide in solution is then generated. This solution is then added to 2 mL of catalyst before concentration. The reduction is total (qualitative test with thiocyanate is negative), but the catalyst must be treated under an inert atmosphere.

This reduction makes it possible to precipitate the $Fe^{2+}$ quantitatively at pH 14; $Zn(OH)_2$ is then converted to $ZnO_2^{2-}$, which is water-soluble, unlike the iron, magnesium and calcium hydroxides in particular. However, the procedure must be carried out under an inert atmosphere and $ZnCl_2$ is regenerated by treatment with 12N HCl. The medium has a high zinc concentration, but the dissolution of $ZnO_2^{2-}$ is impaired because a colloid solution is obtained. The yield is of the order of 40% (Table VIII):

TABLE VIII

| | Catalyst | | | | | | |
|---|---|---|---|---|---|---|---|
| | Mg | Al | Ca | Fe | Zn | Cd | Pb |
| Without $SO_2$ treatment | 11816 | 4726 | 90860 | 8738 | 61040 | 5498 | 12992 |
| With $SO_2$ treatment | 2757 | 4564 | 58372 | 1128 | 89920 | 2324 | 12880 |

By way of comparison and with the same aim of removing the $Fe^{3+}$, liquid-liquid extraction tests with versatic acid and (2-ethylhexyl)phosphoric acid (DEHPA) were carried out according to the following protocol:

A catalytic solution of 0.0005 mol/l is prepared; the pH is adjusted to 2 by the addition of soda; 10 mg of NaCl is added in order to increase the ionic strength of the medium. The organic solution (versatic acid or DEHPA) is prepared at 1M in toluene. 15 mL of aqueous phase and 15 mL of organic phase are stirred for 30 minutes, then the mixture is centrifuged. The aqueous phase is isolated then concentrated and analyzed by ICP-MS. The extraction of iron to the organic phase is evident, but the zinc is also partially entrained (Table IX).

TABLE IX

| | Catalyst | | | | | | |
|---|---|---|---|---|---|---|---|
| | Mg | Al | Ca | Fe | Zn | Cd | Pb |
| Originating from the aqueous phase after extraction of the Fe(III) with versatic acid | 9766 | 556 | 99735 | 936 | 48800 | 3240 | 12880 |
| Originating from the aqueous phase after extraction of the Fe(III) with di(ethyl 2-hexyl)phosphoric acid | 10829 | 50 | 103445 | 350 | 31650 | 8810 | 890 |

1.2.3: Removal of the $Pb^{2+}$ washing with acetone: a simple washing with acetone entrains $Zn^{2+}$ and $Fe^{3+}$ in solution and precipitates a significant portion of lead chloride (Table X).

TABLE X

| | Run | | | | | | | | |
|---|---|---|---|---|---|---|---|---|---|
| | g ng/mL | Mg ppm | Al ppm | Ca ppm | Fe ppm | Cu ppm | Zn ppm | Cd ppm | Pb ppm |
| cat. Thlaspi 12M | 5 g | 14056 | 5121 | 87821 | 13852 | 240 | 95039 | 8307 | 16226 |
| cat insoluble in acetone | 2.25 g | 12162 | 10445 | 109142 | 3998 | 109 | 2617 | 7832 | 38244 |
| cat soluble in acetone | 3.07 g | 14403 | 289 | 70853 | 16032 | 319 | 186032 | 10754 | 221 |

Example 2

Assay of the Zinc in the Leaves of Plants, after Dehydration, by UV-Visible Spectrophotometry (Assay with Zincon, According to CEFE: Centre d'Écologie Fonctionnelle Et Evolutive, Hélène Frérot Et Bruno Buatois)

Subject:

Measurement of the zinc concentration in a plant sample after dissolving the metal in an acid, addition of a colorimetric agent, and analysis by UV-visible spectrophotometry of the intensity of the colouration which depends on the quantity of zinc in the sample.

Definitions:

Zincon=[alpha-(hydroxy-2 sulpho-5 phenylazo)benzylidene]hydrazino-2 benzoic acid, monosodium salt

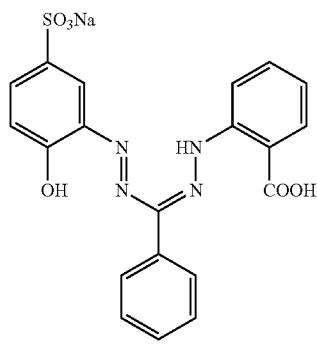

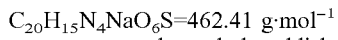

$C_{20}H_{15}N_4NaO_6S = 462.41$ g·mol$^{-1}$

Appearance: purple or dark reddish powder

Absorbance: >0.375 (around 490 nm)

Sulphated ash: 15-25%

Zincon is a chelator of metals (Cu, Zn, Pb, Cd, Fe, Mn, Ni, Co, Al, etc.). The chelation of the zinc takes place at pH 8.5-9.5. At these pHs, the aqueous zincon solution is orange in colour, and changes to blue in the presence of zinc. At 606 nm, the absorbance values of a zinc solution containing zincon give the zinc concentration in the solution.

Absorbance

As illustrated in FIG. 1, the light absorption is demonstrated by a number of photons (light intensity) that is lower when leaving the sample than when entering.

Is−I=−dI=k.c.I.dl which gives dI/I=−k.c.dl which is integrated according to $$\int_{I_o}^{I} \frac{dI}{I} = -kc \int_{0}^{l} dl$$

which gives Ln(I/Io)=−k.c.L.

The absorbance (A) is preferably defined according to A=log (I/Io)=−ϵ.c.L (Beer-Lambert's Law), where c is the molar absorption coefficient (in $M^{-1} \cdot cm^{-1}$). Sometimes the transmission T=I/Io is also used.

It should be noted that 0<T<1 and 0<A<█ and that absorbance is additive, whereas transmission is not.

Principle of the Method:

The method was developed by Macnair & Smirnoff (Commun. Soil Sci. Plant Anal. 1999, 30, 1127-1136) for *Arabidopsis halleri* and *Mimulus guttatus*. It was subsequently used for *Thlaspi caerulescens*. The measurements can be averages (for the entire plant: above-ground part and/or underground part) or one-off measurements (for a piece of leaf or root). The plant samples are digested by sulphosalicylic acid, in which the zinc will dissolve slowly. A buffer solution at pH 9.6 makes it possible to adjust the pH of the samples to values that are compatible with the chelation of the zinc by the zincon. The zincon solution is then added in a set quantity. The sampling is carried out using standard solutions made up of sulphosalicylic acid and zinc sulphate. The quantity of zincon must remain greater than the quantity of zinc in the sample. In this way, the chelator is not saturated, all the zinc content in the sample is capable of being measured, and the absorbance value is situated within the standard range. A blue colouration of the sample after the addition of zincon indicates its saturation, hence the need for dilution before the measurements.

Reagents:

2% Solution of Sulphosalicylic Acid ($C_7H_6O_6S$, $2H_2O$; M=254.21 g·mol$^{-1}$; irritant to eyes and skin; in case of contact with the eyes, wash immediately with plenty of water and take medical advice)

Weigh 20 g of powdered sulphosalicylic acid into a 250 mL beaker

Add pure water and place under magnetic stifling until completely dissolved

Pour into a 1 L (or 500 mL) volumetric flask and top up to 1 L with pure water

Stir the final solution by hand

Buffer Solution pH=9.6

Calibrate the pH-meter (see protocol for use of the pH-meter)

Weigh 7.5 g of potassium chloride (KCl; 74.55 g·mol$^{-1}$) into a 250 mL beaker Weigh 6.2 g of orthoboric acid (H$_3$BO$_3$; M=61.83 g·mol$^{-1}$) into a 250 mL beaker Add pure water to each beaker and place under magnetic stirring until completely dissolved Pour the contents of both beakers into a single 1 L beaker and top up to 800 mL with pure water Place under magnetic stirring and place the electrode of the pH-meter in the solution Prepare 100 mL of 2M a potassium hydroxide solution, i.e. 11.22 g in 100 mL of pure water (KOH; M=56.11 g·mol$^{-1}$; R22-35: harmful if swallowed, causes serious burns; S26-36/37/39-45: in case of contact with the eyes, wash immediately with plenty of water and take medical advice, wear suitable protective clothing).

Using the KOH solution, gradually bring the pH to 9.6 (volume added approximately 50 mL)

Pour 1 L (or 500 mL) into a volumetric flask and top up to 1 L with pure water

Stir the final solution by hand 25 mM Zinc Sulphate (ZnSO$_4$, 7H$_2$O; M=287.54 g/mol; R36/38-50/53: irritant to eyes and skin, very toxic to aquatic organisms, can lead to harmful long-term effects for aquatic organisms; S22-25-60-61: do not inhale dust, avoid contact with the eyes, dispose of the product and its container as a hazardous product, prevent release into the environment)

Weigh 0.719 g of ZnSO$_4$, 7H$_2$O into a 100 mL beaker

Add less than 100 mL of 2% sulphosalicylic acid and place under magnetic stirring until completely dissolved Pour the contents of the beaker into a 100 mL volumetric flask, and top up to 100 mL with sulphosalicylic acid (or weigh 7.19 g and place 10 mL in 100 mL)

0.03% Zincon Solution to be Prepared Just Before Use

Weigh 0.03 g of zincon powder (kept under vacuum in a desiccator) per 100 mL of aqueous solution into a beaker. Add the required volume of pure water and place under magnetic stirring in a desiccator under vacuum until completely dissolved Stir gently by hand before each use (undissolved powder may remain)

Apparatus:

The device used is the Helios γ spectrophotometer. Special 1 mL cells are arranged on a carousel. A light beam of a given wavelength passes through the cells on their polished face. The carousel comprises 7 positions. Position no. 1 receives the reference sample serving to provide the absorbance zero (0 nmol of zinc in the sample). The other 6 positions receive the samples containing the zinc to be assayed. In order to read the absorbance values, it is sufficient to rotate the carousel manually in order to successively arrange the cells opposite the light beam.

Calibration:

Standard Solutions (1 mL Volumes)

Prepare 6 Eppendorf tubes by writing the number of moles in 20 μL (volume of a sample) of standard solution Distribute the different volumes of 25 mM stock solution into the tubes, using a 20-200 μL pipette, using a different tip for each tube Top up the volumes to 1 mL with 2% sulphosalicylic acid using a 100-1000 μL pipette Constructing the Calibration Line 1. Turn on the spectrophotometer using the button at the rear of the device.
2. Wait until the device has carried out all the tests.
3. Adjust the wavelength by pressing the button corresponding to λm then enter the wavelength+ENTER.
4. Check that the device is in absorbance mode (in MODE select ABS).
5. Place 780 μL of buffer solution in each 1 mL cell, using the 100-1000 μL pipette.
6. Add 200 μL of zincon using the 20-200 μL pipette; the colour of the mixtures varies from orange to blue (blue=saturation of the chelator).
7. Add 20 μL of standard solution using the 20-200 μL pipette.
8. Homogenize the mixture in each cell using the 20-200 μL pipette and the tips that were used for sampling the standard solutions.
9. Place the cells on the carousel of the spectrophotometer (take care with the orientation with respect to the light beams), such that the "0 nmol" cell is in position no. 1, "10 nmol" in position no. 2, etc.
10. Press on "zero base", the device zeros the absorbance for cell no. 1
11. Turn the carousel anticlockwise one position, the absorbance is then indicated for cell no. 2, etc. up to cell no. 7.
12. Check that the absorbance as a function of the concentration of the standard solution follows a linear relationship (Beer-Lambert law), and note the gradient of the line.
13. Optionally, take replicates; check the pH of 10 mL of mixture for spectrophotometry, for 0, 40 and 80 nmol.
14. The gradient of this line is used for calculating the zinc content of the samples. The gradient is the denominator.

Sampling:

Preparation of the Samples for Estimating the Average Zinc Concentration:

Cut the plant portion for analysis (leaves or roots) into small fragments (fresh matter) or grind dry with a mortar (dry matter) for each individual plant Mix the fragments and distribute into several Eppendorf tubes (at least 4 per individual plant), at a rate of 50 to 100 mg of material per Eppendorf tube (approximately half filling); the mass of the samples is measured accurately by setting the scales to zero for each Eppendorf tube before weighing a sample If the plant matter is fresh, make a small hole in the stopper of the Eppendorf tubes before immersing them for 30 minutes in liquid nitrogen (allow to float in a polystyrene container closed with a lid)

Add 1000 to 1500 μL of 2% sulphosalicylic acid: the lower volumes are used when the mass of tissues is low and when the expected zinc concentration is low Allow the digestion of the tissues by the acid to take place overnight Dilution: take 100 microlitres of the sample and pour it into another Eppendorf tube. Then add 300 microlitres of sulphosalicylic acid in order to obtain a ×4 dilution. 700 microlitres must be added for a ×8 dilution.

Preparation of the Samples for One-Off Measurements:
  Cut the plant portion for analysis (leaves or roots) into small fragments (fresh matter) or grind dry with a mortar (dry matter) for each individual plant
  Place the fragments in an Eppendorf tube at the rate of 5 to 50 mg of material per Eppendorf tube; the mass of the samples is measured accurately by setting the scales to zero for each Eppendorf tube before weighing a sample
  If the plant matter is fresh, make a small hole in the stopper of the Eppendorf tubes before immersing them for 30 minutes in liquid nitrogen (allow to float in a polystyrene container)
  Add 1000 to 1500 µL of 2% sulphosalicylic acid: the lower volumes are used when the mass of tissue is low and when the expected zinc concentration is low
  Allow the digestion of the tissues by the acid to take place overnight
  Dilution: take 100 microlitres of the sample and pour it into another Eppendorf tube. Then add 300 microlitres of sulphosalicylic acid in order to obtain a ×4 dilution. 700 microlitres must be added for a ×8 dilution.

Operating Method:
  1. Switch on the spectrophotometer
  2. In each 1 mL cell:
  3. Place 780 µL of buffer using the 100-1000 µL pipette
  4. Add 200 µL of freshly prepared zincon using the 20-200 µL pipette
  5. Take a 20 µL sample using the 20-200 µL pipette; if necessary in order to sample a clearer liquid, centrifuge the Eppendorf tube at 10000 rpm for approximately 8 minutes
  6. Homogenize the mixture in each cell using the 20-200 µL pipette and the tips that were used for taking the samples.
  7. Note the colour of the sample; if necessary (blue solution=saturated chelator) dilute the sample while trying to take as much of it as possible during the dilution
  8. Measure the absorbance at 606 nm by spectrophotometry, and deduce therefrom the zinc content of the sample (in nmol) by means of the calibration line Important Note:
Zincon is sensitive to oxidation, therefore store the powder protected from air (in a vacuum bell jar), protect the solution ready for use, and do not keep it for more than one day.

Example 3

Reactions with the Zinc Catalyst of Example 1

3.1: Halogenation of the Alcohols with a Catalyst the Metal of which is Zn
  Example of the Secondary Alcohols (General Procedure):
  From 0.5 to 2 mmoles, in particular 1 mmole of alcohol (depending on the alcohol used) is added to the reaction mixture of Example 1.1 or 1.2 at 25° C.
  The average stifling time is 8 hours at 20° C. The chlorinated derivative can be isolated by the addition of petroleum ether, extraction, washing with a solution of sodium hydrogen carbonate, drying over calcium chloride and removal of the petroleum ether.
  A Beilstein test and GC MS analysis (VARIAN Chrompack CP 3800 Gas Chromatography/Varian MS Saturn 2000-Column optima 5; 30 m-0.25µ-flow rate: 1 mL/min-Programme: 50° C.: 2 minutes/100° C. (increase: 5° C./min); 12 minutes/150° C.); (increase: 20° C./min); 150° C.: 16 min; (increase: 50° C./min); 250° C.: 17 min) confirm the formation of the chlorinated derivative.

Extension of the Method to the Tertiary and Secondary Benzyl Alcohols:
  These alcohols were tested under the same conditions. The reaction is rapid (30 minutes).

Extension of the Method to the Primary Alcohols:
  The method is comparable, but the chlorination reaction is more difficult. Heating at a high temperature (reflux of the reaction medium) was carried out for 10 hours.
  Table XI below shows the same reactions carried out with a catalyst obtained with 12N HCl, used crude (Example 1.1) or purified (Example 1.2) as well as a comparison with the Lucas reaction carried out according to the standard conditions well known to a person skilled in the art:

TABLE XI

| | 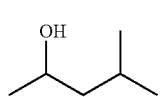 | 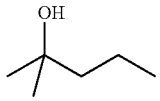 | 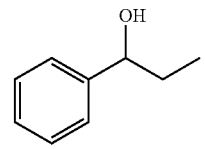 | 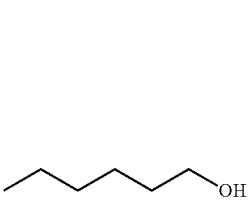 | 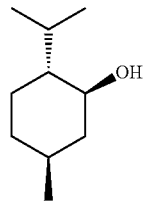 |
|---|---|---|---|---|---|
| MW | 102.10 | 102.10 | 136.09 | 102.10 | 156.27 |
| Number of moles | 0.5 to 2 mmol | 0.7 to 1 mmol | 0.7 to 1 mmol | 0.7 to 1 mmol | 1 mmol |
| Conditions and catalyst used | Catalyst purified on Amberlyte resin 10 h to 25° C. | Crude catalyst 10 hours at 25° C. | Crude catalyst 10 hours at 25° C. | Catalyst purified on Amberlyte resin 10 hours at 25° C. | Catalyst purified on Amberlyte resin 10 hours at 25° C. |
| Products obtained and yield | 2-chloro-4-methyl pentane: 54% 2-chloro-2-methyl pentane: 44% 3-chloro-3-methyl pentane: <1% 2-methyl-pentan-2-ol: 2% | 2-chloro-2-methyl pentane: 47% 3-chloro-3-methyl pentane: 53% | 1-chloro-1-phenyl propane: 90% | 1-chloro-1-hexane: 28% 2-chloro-1-hexane: 15% | Chloromenthane: 94% Menth-3-ene: 5% Menth-2-ene: 1.5% Bicyclo Menthol: 0% |

TABLE XI-continued

| | 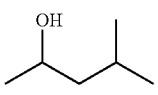 | 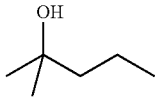 | 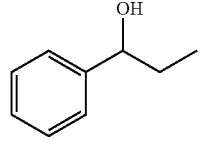 | 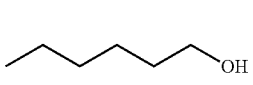 | 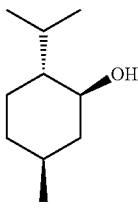 |
|---|---|---|---|---|---|
| Comparison with the Lucas standard reaction | 8 hours at 25° C. 2-chloro-4-methyl pentane: 54% 2-chloro-2-methyl pentane: 44% 3-chloro-3-methyl pentane: <1% 2-methyl-pentan-2-ol: 2% | 8 hours at 25° C. 2-chloro-2-methyl pentane: 47% 3-chloro-3-methyl pentane: 53% | 2 hours at 25° C. 1-chloro-1-phenyl propane: 100% | | Chloromenthane: 94% Menth-3-ene: 5% Menth-2-ene: 1.5% Menthol: 0% |

3.1: Electrophilic Aromatic Substitution
The catalyst used is crude (Example 1.1 with 12N HCl)
It must be dispersed on montmorillonite or silica impregnated with metal oxide
It can be recycled at least four times.
3.1.1: Friedel-Crafts Alkylation
217 mg of dry crude catalyst (Example 1.1 with 12N HCl) is dispersed and ground in a mortar with 174 mg of Montmorillonite K10, then heated to 110° C. in a crucible.

The halogenated derivative (87 mmol) is added to 20 equivalents of the aromatic reagent.

The previous solid is added in one go. The mixture is stirred for the time given in the table. The medium is filtered, then concentrated under vacuum. The medium is analysed by GC-MS and $^1$H NMR.

The results are shown in Table XII below:

TABLE XII

| Compound A | Compound B | conditions | Yields of regiomers | comments |
|---|---|---|---|---|
| 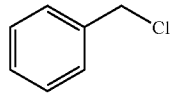 | 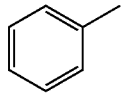 | 1 hour | 2.5% | Many by-products 2 of which are adducts of Zn |
| 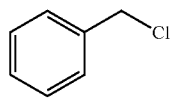 | 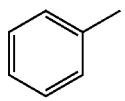 | 1 hour | 11% | |
| 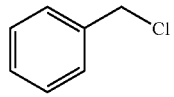 | 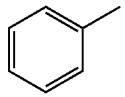 | 1 hour | 100% Ortho: 18% Para: 82% | |
| 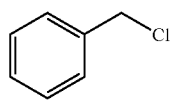 | 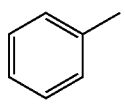 | 1 hour | 100% Ortho: 18% Para: 82% | Recycled catalyst |
| 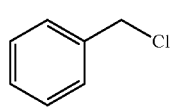 | 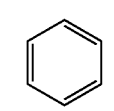 | 1 hour 9 h 14 h | 30% 52% 69% | |
| 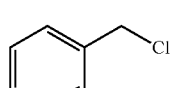 | 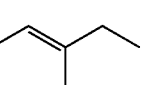 | 1 hour 14 h | 0% 89% Ortho: 31% Para: 69% | |

TABLE XII-continued

| Compound A | Compound B | conditions | Yields of regiomers | comments |
|---|---|---|---|---|
| 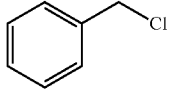 | 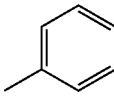 | 1 hour<br>14 h | 52%<br>98% | |
| 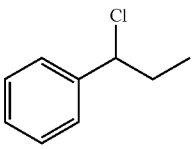<br>originating from the previous Lucas reaction (Example 3, table XI) | 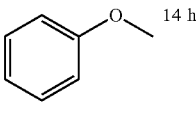 | 14 h | 31%<br>Ortho: 30%<br>Para: 70% | |
| 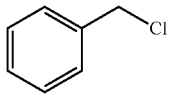 | 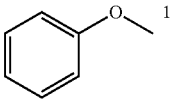 | 10 min | 100%<br>Ortho: 40%<br>Para: 60% | |

3.1.2: Friedel-Crafts Acylation

Colouring Agents:

Phenolphthalein 500 mg of phthalic anhydride, 500 mg of phenol and 1 g of crude catalyst derived from *Thlaspi* (Example 1.1, 12N HCl) dehydrated at 110° C. for a few minutes are placed in a single-necked flask and heated at 80° C. for 5 minutes.

After cooling down, the reaction mixture is diluted in 5 mL of a water/ethanol mixture. 1 mL of solution is taken then added to a 3M soda solution.

In the case of phenolphthalein, the solution becomes pink immediately.

After washing with ether, the phenolphthalein crystallizes easily.

Fluorescein 500 mg of phthalic anhydride, 500 mg of resorcinol and 2 g of crude catalyst derived from *Thlaspi* (Example 1.1, 12N HCl) dehydrated at 110° C. for a few minutes are placed in a single-necked flask and heated at 80° C. for 5 minutes.

After cooling down, the reaction mixture is diluted in 5 mL of a water/ethanol mixture. 1 mL of solution is taken then added to a 3M soda solution.

For fluorescein, the basic mixture is poured into a dilute ammonia solution. A bright fluorescent yellow solution shows that fluorescein has been formed.

Ortho or Para Ethyl Acetophenone

Place 5 mL of anhydrous toluene in a three-necked flask, then introduce 4.5 g of catalyst (Example 1.1, 12N HCl) in one go. Add 0.7 mL of acetic anhydride dropwise. Heat for 30 minutes at 100° C. Leave to cool down and pour the reaction mixture onto an ice-cold solution of concentrated hydrochloric acid (10 mL). Pour into a separating funnel, then separate the organic phase. Wash the latter with water, then with an aqueous solution of ammonium chloride at pH=7.

Dry the organic phase over anhydrous sodium sulphate.

The results are shown in Table XIII:

TABLE XIII

| Compound A | Compound B | conditions | Yields of regiomers | comments |
|---|---|---|---|---|
| 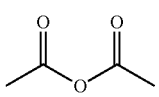 | 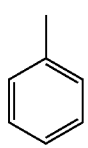 | 30 min | 95%<br>Ortho: 40%<br>Para: 60% | |
| 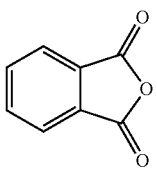 | 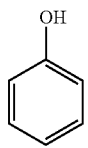 | 5 min | 90% | Extraction with ether<br>Mp° C.: 258-263<br>Colour test at pH 9 |

TABLE XIII-continued

| Compound A | Compound B | conditions | Yields of regiomers | comments |
|---|---|---|---|---|
| 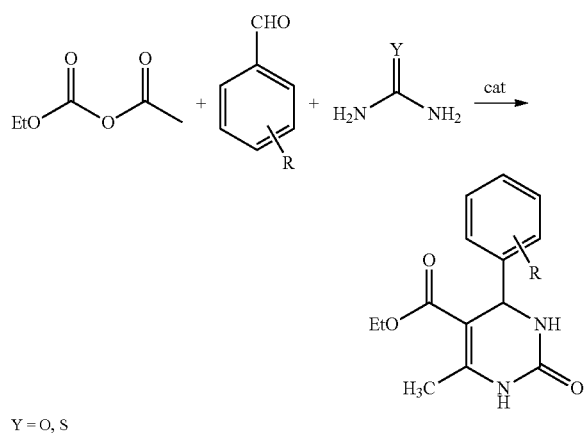 | | 5 min | 90% | Washing with EtOH 20° C.- showing fluorescence under UV |

3.2: Synthesis of 3,4-dihydropyrimidin-2(1H)-one or 3,4-dihydropyrimidin-2(1H)-thione (Biginelli Reaction)

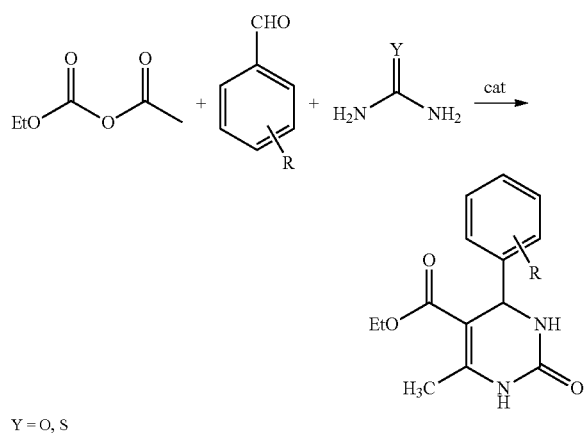

Y = O, S

Protocol:

3 g of zinc dichloride originating from the catalyst derived from *Thlaspi* (Ganges Ecotype), purified on Amberlyte resin (Example 1.2.1) and dehydrated (110° C., 2 hours)) is dispersed in 10 g of K100 silica. The mixture is finely ground and placed in 60 mL of anhydrous toluene. The reaction mixture is brought to reflux for 10 hours, filtered and the solid residue is heated at 110° C. for 12 hours. A solution of 2.5 mmol of benzaldehyde, 2.5 mmol of urea (or of thiourea) diluted in 15 mL of anhydrous acetonitrile is then added. The mixture is brought to reflux for 10 hours. The reaction is easily monitored by TLC (UV development-eluent: pure diethyl ether) and the mixture is filtered. It is purified by crystallization from the EtOAc-hexane mixture. The yield is 80%. The pure product is characterized by its melting point, $^1$H NMR, $^{13}$C NMR, COSY and HSQC and IR.

3.3: Cycloaddition Reactions

Diels-Alder: Cyclopentadiene and Diethyl Fumarate)

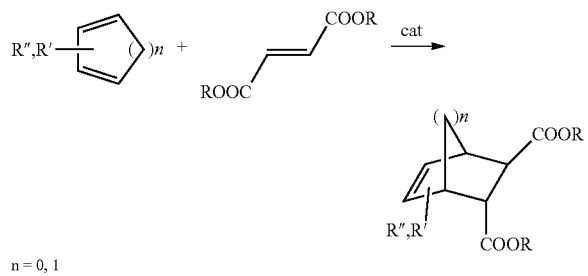

n = 0, 1

Protocol:

A 1M solution of catalyst derived from *Thlaspi* (Ganges Ecotype), purified on Amberlyte resin (Example 1.2.1) and dehydrated (150° C., 2 hours) is prepared in anhydrous toluene. This solution is added to a solution of diethyl fumarate (2.5 mmol) in 15 mL of toluene. After stifling for 30 minutes, freshly distilled cyclopentadiene (3 mmol) is added. The reaction mixture is stirred for 15 minutes, then the solution is hydrolyzed by a saturated aqueous solution of sodium hydrogen carbonate.

The aqueous phase is extracted with ether (3×20 mL). The organic phases are combined, dried over sodium sulphate and concentrated under vacuum.

The adduct is characterized by GC-MS, $^1$H and $^{13}$C NMR. The reaction is quantitative and perfectly diastereoselective: no isomerization is observed.

The stereoselectivity of the reaction was studied on menthyl fumarate:

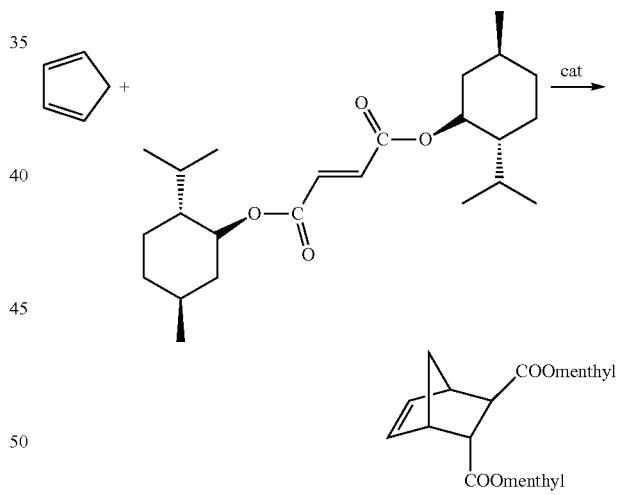

The reaction is quantitative after stirring for 1 hour at −20° C.

The diastereomeric ratio is 2.3.

This result has not been optimized and can be optimized by adjusting the quantity of catalyst and by studying the effect of the solvent.

3.4: Transesterification Reactions

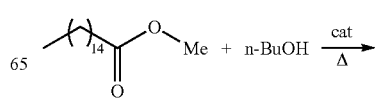

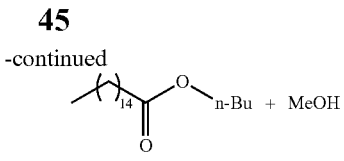

A reaction model was studied with methyl palmitate (270 mg, 1 mmol) and butan-1-ol (5 mL). 100 mg of dehydrated catalyst originating from *Thlaspi* was added; the mixture was heated for 5 hours, then 10 hours and analyzed by GC-MS.

If the catalyst is used in the crude state (Example 1.1, 12N HCl), the reaction exhibits a degree of conversion of 13%.

If it is purified with amberlyte resin (Example 1.2.1), it is 60%.

Example 4

Modelling a Halogenation Reaction Carried Out in a Metallophyte Species

1) Preparation of zinc malate, in order to cultivate the species in which zinc is present, T. caerulecens, in the laboratory;
2) Preparation of zinc chloride from zinc malate;
3) Halogenation of a secondary alcohol using the zinc chloride prepared previously.

Implementation of these transformations is carried out as follows:

1) the zinc malate is prepared by the action of activated powdered zinc (prior activation by Me$_3$SiCl) on malic acid (Aldrich 088K0026). As the latter is solid, a partial dissolution and homogenization of the medium are carried out using 4-methyl-pentan-2-ol. This alcohol acts both as a solvent throughout the method and as a specimen alcohol in the halogenation reaction; the release of hydrogen, then the total dissolution of the zinc make it possible to follow the progress of the reaction.

The reaction requires heating to 50° C. in order to ensure total zinc consumption, a condition necessary so that the reaction sequence is significant (otherwise the zinc reacts with HCl in the following step to form ZnCl$_2$ directly).

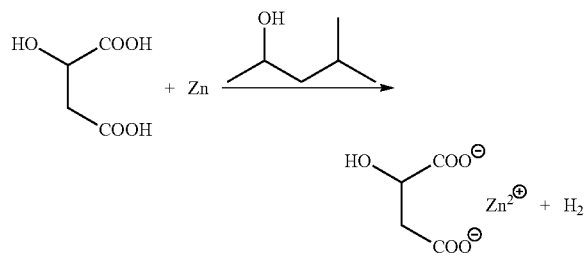

2) the addition of an excess of hydrochloric acid to the zinc malate allows the zinc dichloride to be formed by simple acid-base reaction and results in the in situ preparation of the Lucas reagent.

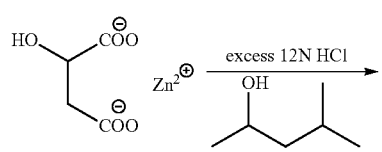

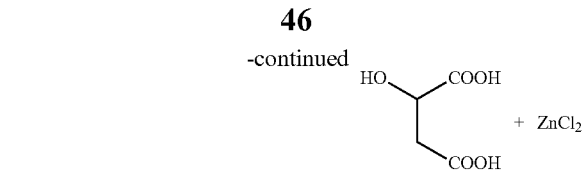

3) As the ZnCl$_2$/HCl mixture is formed in the presence of 4-methyl-pentan-2-ol, the halogenation reaction starts as soon as HCl is added.

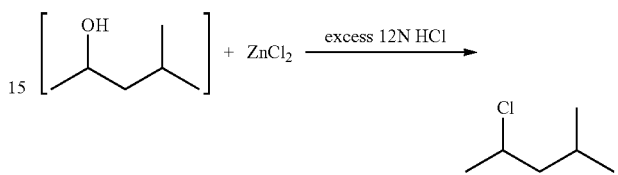

After stirring for 15 minutes at ambient temperature, the reaction mixture is treated. The conversion rate evaluated by GC MS is 60%.

Conclusion

The reaction sequence carried out in a plant medium is therefore perfectly modelled under standard synthesis conditions.

Experimental Part 2.534 g of malic acid (0.0189 mol) in solid form, as well as 2.472 g of zinc metal (0.018 mol) in powder form are successively introduced into a 100 mL single-necked flask provided with water-cooled condenser, and 4-methyl-pentan-2-ol (7 mL) is added in order to disperse the solids and facilitate the stifling of the reaction medium in which the malic acid is partially soluble.

The mixture is taken to reflux for 4 hours at 50° C., then it is returned to ambient temperature under stifling for 12 hours until all of the zinc metal has been consumed.

12N hydrochloric acid (6 eq.) is then added to the mixture in order to produce ZnCl$_2$.

Finally, the excess of 4-methyl-pentan-2-ol reacts with the regenerated malic acid in order to produce 2-chloro-4-methyl-pentane. 15 mL of ether is added to extract the chlorinated derivative. After decantation and separation of the aqueous and organic phases, the ether phase is washed twice with 10 mL of water then dried over magnesium sulphate. The solution is filtered then concentrated. The crude mixture is distilled (bp=131-134° C.). 60% of 2-chloro-4-methylpentane (1.285 g) is isolated pure.

The solution is subjected to the Beilstein test in order to indirectly check the presence of ZnCl$_2$. The test is positive. The formation of the chlorinated derivative is easily confirmed by mass spectrometry (m/z: 135 and 137).

Example 5

Preparation of a Composition Containing a Metal Catalyst the Metal of which is Ni Example 5.1

*Sebertia acuminata* plant 10 g of stems and twigs of Sebertia *acuminata* are calcined. 4.5 to 5 g of nickel is thus obtained. The ash is placed in a beaker containing 30 mL of 12N HCl. The mixture is stirred vigorously for 30 minutes at 50° C.

The mixture is filtered, then the filtrate is concentrated and dehydrated at 110° C. in order to obtain a dehydrated composition containing an $NiCl_2$ catalyst.

Example 5.2

*Psychotria douarrei* Plant

Calcining:

The calcining is carried out according to the standard programme (300° C. for 2 hours, then 550° C. for 3 hours).

Preparation of the Catalyst:

1 g of *Psychotria douarrei* ash is taken. A minimum of 12N HCl is added to the ash (approximately 20 mL); all of the solid passes into solution and rapidly becomes a pale green colour. After 2 hours at 60° C., the mixture is evaporated at 80° C., filtered and produces 1 g of a fine powder having a pale yellow colour, the colour of dehydrated nickel dichloride.

Results of ICP-MS (Table XIV):

TABLE XIV

|  | Mg | Al | Ca | Fe | Cu | Zn | Cd | Pb | Mn | Ni |
|---|---|---|---|---|---|---|---|---|---|---|
| Ash | 87020 | 880 | 105945 | 260 | 4740 | 7040 | 20 | 300 | 260 | 185600 |
| Crude catalyst | 78240 | 1620 | 93719 | 1760 | 4560 | 5760 | 14 | 360 | 1160 | 270320 |

Figure 4:
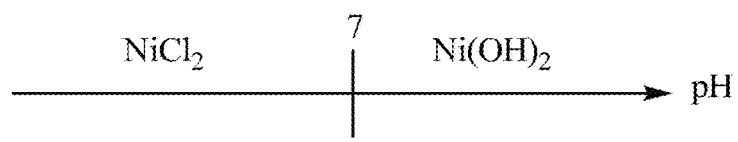
FIG. 4 illustrates the selective precipitation of catalytic compound as function of pH.

Selective Precipitation:

Principle:

See FIG. 4

Precipitation is carried out at pH=7 by adding 1M soda to 100 mg of catalytic solid diluted in 2 mL of 1M HCl. The precipitate appears from pH ~6.5

The heterogeneous solution is centrifuged, dried (100 mg recovered) and analyzed by ICP-MS (5 mg/50 mL of 2.5% $HNO_3$). The solid is pale green.

Results of ICP-MS (Table XV):

TABLE XV

| | Catalyst | | | | | | | | | |
|---|---|---|---|---|---|---|---|---|---|---|
| | Mg | Al | Ca | Fe | Cu | Zn | Cd | Pb | Mn | Ni |
| Precipitated at pH = 7 | 9237 | 1500 | 62019 | 640 | 4660 | 5800 | 30 | 300 | 540 | 331028 |

The crude catalyst (Example 5.2) has been the subject of developments in organic synthesis.

It is very efficient:

the test electrophilic aromatic substitution reaction between toluene and benzyl chloride (Cf. operating method described with K10 montmorillonite, Example 3.1.1) is 80% after reaction for 1 hour at 20° C.

the Diels-Alder reaction between diethyl fumarate and cyclopentadiene is very rapid: it is completed after stirring for 15 minutes at 20° C.; this result opens up new prospects for asymmetric synthesis. The efficiency of the catalysis by nickel dichloride and the ease of the reaction make it possible to carry out tests at a low temperature in order to promote high asymmetric induction with dimenthyl fumarate.

The Biginelli reaction is also possible and comparable to the previous tests. It is comparable to the test with pure hydrated $NiCl_2$ described in the literature (Jun Lu, Yinjuan bai, Synthesis 2002, 4, 466).

These results are original, as with the exception of the Biginelli reaction, $NiCl_2$ is rarely used in Lewis acid catalysis.

Figure 5:
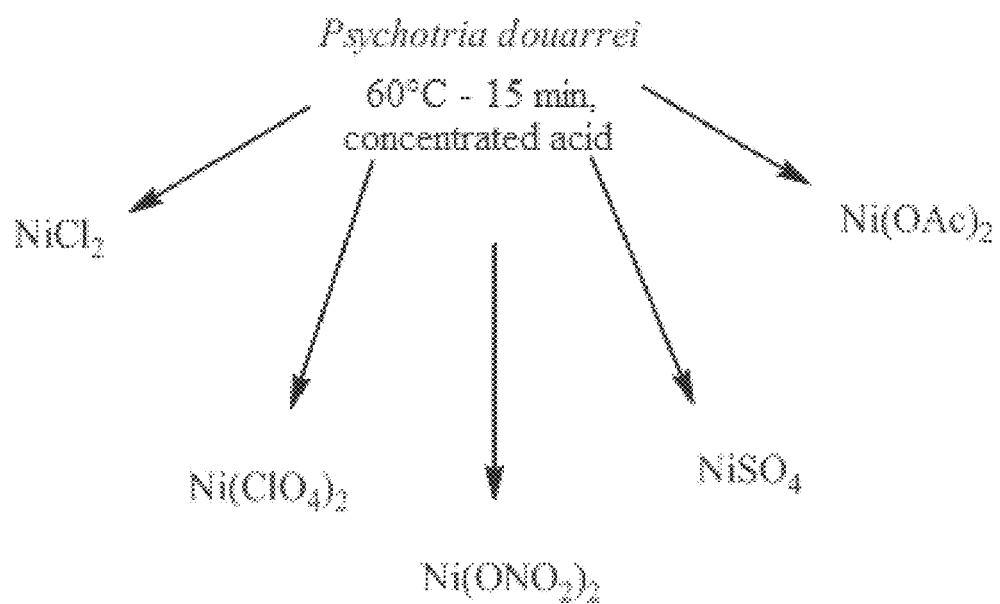
FIG. 5 illustrates the preparation of different nickel salts from a single precursor: *Psychotria douarrei*.

An advantage of the method is that the treatment of the plant makes it possible to produce different nickel salts from a single precursor: *P. douarrei*. The benefit is to have available catalytic systems of different solubility and varying applications. The successful tests are as follows:

See FIG. 5

Example 6

Preparation of Dichlorbis(Triphenylphosphine)Nickel(II), an Arynic Coupling Catalyst The composition of Example 5.1 ($NiCl_2$, $6H_2O$) is taken up in 50 mL of dry ethanol and heated to 80° C.

Triphenylphosphine (11 g) is dissolved in 100 mL of dry isopropanol under a nitrogen atmosphere. The mixture is stirred under reflux until the triphenylphosphine is completely dissolved. It is then added to the hot nickel dichloride solution ($NiCl_2$) prepared above. The solution is stirred under reflux for 30 minutes then brought to ambient temperature.

The mixture is filtered then the residual solid is washed with cold ethanol (40 mL), then ether (20 mL). The solid, dichlorobis(triphenylphosphine)nickel(II), is dried under a flow of nitrogen.

Example 7

Preparation of Nickel (0) from the $NiCl_2$ Catalyst of Example 5.1 Isolated from *Sebertia acuminata*

2 g of dehydrated $NiCl_2$ (Example 5.1) is placed in 50 mL of 95% ethanol, then heated to 80° C. until maximum dissolution of the salts. 1 mL of a 6N hydrochloric acid solution is added. 2.5 g of aluminium in grains (100 microns) is added in small portions (0.5 grams at a time) at a rate which makes it possible to maintain the release of dihydrogen. If the green nickel salts are not completely consumed after all the aluminium has been added, a few additional grains are added. The mixture is filtered immediately on a frit. The solid (Ni(0)) is poured rapidly into a soda solution (50 mL of 20% NaOH). Stirring is maintained for 30 minutes at 60° C. The excess soda is removed and the catalytic solid is washed 5 times with 50 mL of distilled water.

Example 8

Reduction of 1-phenyl 2-nitroprene in 1-phenyl 2-aminopropane

This method illustrates an application of the method in the double reduction of a C=C double bond and the nitro group.

2.5 g of 1-phenyl 2-nitropropene are placed in 25 mL of ethanol then added to an ethanolic nickel solution (2 g $NiCl_2$ (Example 5.2) in 50 ml of EtOH).

1.5 mL of hydrochloric acid are added slowly, then 10.5 grams of aluminium are introduced slowly. After dissolution of the aluminium, 4 mL of HCl then 0.8 g of aluminium are added alternately.

Repeat this successive addition of HCl and aluminium twice.

The consumption of the aluminium is slow and needs 5 to 6 hours of reaction. The medium is then neutralized carefully using an aqueous soda solution. The reaction is highly exothermic.

After 30 minutes, the organic phase becomes orange, which indicates the formation of the expected amine. After decantation and concentration, the crude syrup obtained is taken up in acetone.

The addition of sulphuric acid precipitates the ammonium sulphate derived from the 1-phenyl 2-aminopropane, which is isolated by filtration. The overall yield of 1-phenyl 2-aminopropane is 65%.

Example 9

Preparation of a Composition Containing a Metal Catalyst, the Metal of which is Cu 9.1: Catalyst Originating from *Ipomea alpina*

The catalyst is prepared in the same way as for the Zn or the Ni, from *Ipomea alpina* (12N HCl).

9.2: Catalyst Originating from *Bacopa monnieri*

Cultures and accumulation of Cu(II) (CuSO$_4$) according to S. Sinha and P. Chadra, Water, Air and Soil Pollution 51:271-276, 1990.

Calcining:

4 plants having accumulated copper sulphate for 8 days are washed copiously (significant calcareous deposit), dried with filter paper then placed in an oven for 2 hours at 65°. The calcining is then carried out according to the standard programme (300° C. for 2 hours, then 550° C. for 3 hours).

Preparation of the Catalyst:

140 mg of ash is taken. A minimum amount of 1N HCl is added to the ash (approximately 2 mL); after an effervescence of short duration, almost all of the solid passes into solution; the solution rapidly becomes clear and becomes grey-yellow, which makes it possible to assume the formation of copper chloride. The solution is even yellow-green after stirring for 2 hours. After rapid filtration, the mixture is evaporated at 80° C. and leads to 475 mg of a fine rust-coloured powder (Table XVI):

TABLE XVI

| | Run | | | | | | | |
|---|---|---|---|---|---|---|---|---|
| | Mg ppm | Al ppm | Ca ppm | Fe Fe | Cu ppm | Zn ppm | Cd ppm | Pb ppm |
| Cat. *Bacopa* | 8114 | 5496 | 125880 | 5676 | 30060 | 2328 | 412 | 1578 |

9.3: Catalyzed Hydrolysis of Thiophosphates

Figure 2:
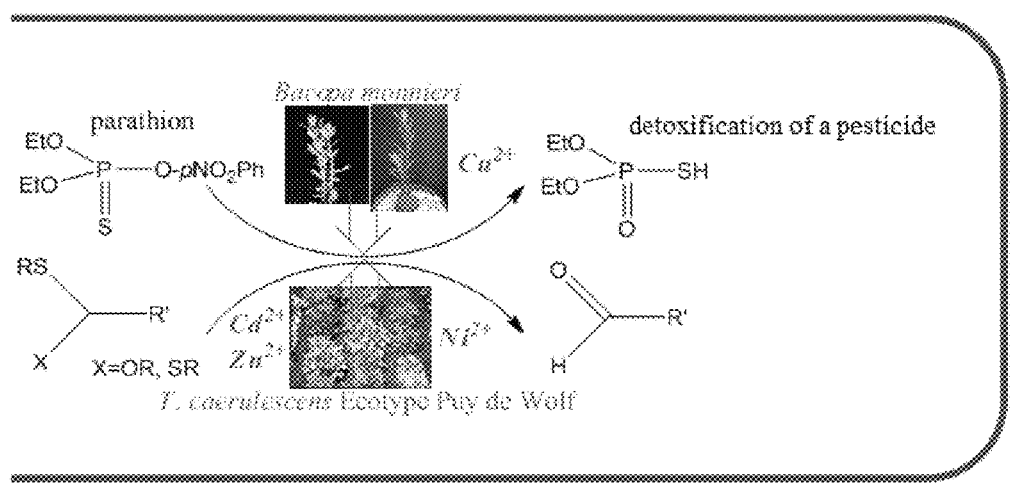
FIG. 2 schematically illustrates the catalyzed hydrolysis of thiophosphates utilizing catalysts prepared from *Bacopa monnieri* or *Thlaspi caerulescens*.

The catalyzed hydrolysis of thiophosphate is illustrated in FIG. 2, in which parathion is detoxified by a catalyst prepared from *Bacopa monnieri* or *Thlaspi caerulescens*.

2 mL of a 1:1 water/ethanol solution at pH=8.0 is introduced into a 5 mL flask.

140 mg of catalyst (Example 9.2) is added to the present solution.

The mixture is stirred at 40° C.

5.5 µL of parathion (stored at 5° C.) is added using a GC micro-syringe through a septum. Stirring is maintained for 30 minutes at 40° C.

The equipment contaminated with parathion (micro-syringe) is washed with 3 M soda, in order to remove the parathion.

The decomposition of the parathion is monitored by $^{31}$P NMR: it proceeds more quickly and further than without *Bacopa* [(EtO)$_2$P(O)O$^-$: +20% in 30 hours including 12% diethyl phosphate].

The reaction can also be carried out by a crude catalyst originating from *Thlaspi caerulescens* (Puy de Wolf Ecotype) obtained as in Example 1.1 but with a lower yield.

Example 10

Development of Oximes

Example 10.1

A 0.5% CuCl$_2$ solution (Example 9.1) in water is prepared and vaporized on an oxime previously deposited on a silica-covered thin-layer chromatography plate.

A green-brown mark appears easily. It is characteristic of the oxime-Cu$^{2+}$ complex.

Example 10.2

A 0.5% CuCl$_2$ solution (Example 9.2) in water is prepared and 2 mL of the solution obtained is placed in a test tube (pale grey-green solution). A few mg of benzaldehyde-oxime (E) are added to the solution. After stirring for a few seconds, a dark green complex appears clearly, characteristic of the oxime-Cu$^{2+}$ complex.

Example 11

Electrophilic Aromatic Substitution Reaction by a Metal Catalyst Isolated from Plants Accumulating Metals Such as Zn, Cu or Ni The catalyst obtained in Example 1 (ZnCl$_2$), Example 5 (NiCl$_2$) or Example 9 (CuCl$_2$) is dehydrated by heating at 110° C., then impregnated with montmorillonite (2 g of montmorillonite per 1.46 g of ZnCl$_2$ for example). The mixture is at 110° C. for 1 hour.

The ZnCl$_2$-montmorillonite catalytic complex is added to the toluene mixture (20 mL) and benzyl chloride (1.27 g).

After stirring for 1 hour, the mixture is filtered and the filtrate washed with hexane. The isomeric electrophilic substitution products, 4- and 2-methyldiphenylmethane are obtained quantitatively.

Example 12

Comparative Example of a Halogenation Reaction of a Secondary Alcohol Carried Out with a Composition Containing a Catalyst, Obtained without Filtration (Step d.)

30.03 g of dehydrated and powdered leaves of *Thlaspi caerulescens* originating from the soil of the mine of Avinières are assayed by the zincon method. The level of zinc present in the dry matter obtained is 420 mg or 2 mmoles. The dry matter is then placed in 20 mL of 1N hydrochloric acid.

The solution is stirred for 1 hour, then sonicated for 2 hours. 1 to 2 mL of 12N HCl is added in order to allow satisfactory stirring of the medium.

2 mmoles of 4-methyl pentan-2-ol are added directly, without filtration, to the previous reaction mixture at 25° C. A very heterogeneous dark green solution is stirred for 5 hours at 40° C., a sample of the reaction medium is place in a few mL of petroleum ether and analyzed by GC MS. Only traces of chlorinated derivative are observed.

The invention claimed is:

1. A method for the implementation of an organic synthesis reaction, comprising:
   providing a composition comprising at least one metal catalyst containing a metal in the M(II) form, said metal originating from a calcined plant or calcined plant part, said composition having been acid treated, wherein said at least one metal in the M(II) form is selected from the group consisting of zinc (Zn), nickel (Ni), manganese (Mn), lead (Pb), cadmium (Cd), calcium (Ca), magnesium (Mg), and copper (Cu); and
   bringing the composition into contact with at least one chemical compound capable of reacting with said composition.

2. The method according to claim 1, wherein the organic synthesis reaction is selected from halogenations, electrophilic aromatic reactions in series, synthesis of 3,4-dihydropyrimidin-2(1H)-one or 3,4-dihydropyrimidin-2(1H)-thione, cycloaddition reactions, transesterification reactions, catalyst synthesis reactions for coupling or hydrogenation reactions after reduction of Ni(II) to Ni(0), synthesis of amino acid or oxime developers, and hydrolysis of sulphur-containing organic functions.

3. The method of claim 1, wherein said organic synthesis reaction is selected from halogenation of alcohols, electrophilic aromatic reactions in series, selected from substitutions or additions; catalyst synthesis reactions for coupling or hydrogenation reactions after reduction of Ni(II) to Ni(0), synthesis of 3,4-dihydropyrimidin-2(1H)-one or 3,4-dihydropyrimidin-2(1H)-thione, cycloaddition reactions, and synthesis of amino acid or oxime developers.

4. The method according to claim 1, wherein the organic synthesis reaction is the halogenation of primary, secondary or tertiary alcohols.

5. The method according to claim 1, wherein the organic synthesis reaction is an electrophilic reaction in series selected from electrophilic substitutions and additions.

6. The method according to claim 1, wherein the organic synthesis reaction is a Diels-Alder cycloaddition.

7. The method according to claim 1, wherein the organic synthesis reaction is a coupling reaction in the synthesis of diaryl compounds.

8. The method according to claim 1, wherein the organic synthesis reaction is the catalyzed hydrolysis of thiophosphates.

9. The method according to claim 1, wherein the metal is selected from zinc (Zn), nickel (Ni) and copper (Cu).

10. The method according to claim 1, wherein the metal is selected from zinc (Zn), nickel (Ni), manganese (Mn), lead (Pb) and cadmium (Cd).

11. The method according to claim 1, wherein the acid treatment is carried out by hydrochloric acid.

12. The method according to claim 1, wherein said plant is from the Brassicaceae family.

13. The method according to claim 1, wherein said plant is *Anthyllis vulneraria, Thlaspi caerulescens* or *Arabidopsis hallerii* and the metal is Zn.

14. The method according to claim 13, wherein the Zn concentration in the plant is from 2700 mg/kg to 43700 mg/kg of dry weight of plant or plant part.

15. The method according to claim 1, wherein said plant belongs to the Sapotaceae family and the metal is Ni.

16. The method according to claim 15, wherein the Ni concentration in the plant is from 1000 mg/kg to 36000 mg/kg of dry weight of plant or plant part.

17. The method according to claim 1, wherein said plant belongs to the Convolvulaceae family and the metal is Cu.

18. The method according to claim 17, wherein the Cu concentration in the plant is from 1000 mg/kg to 13700 mg/kg of dry weight of plant or plant part.

19. The method according to claim 1, wherein the composition is devoid of or contains only traces of chlorophyll.

20. The method according to claim 1, wherein said plant is *Psychotria douarrei* and the metal is Ni.

21. The method according to claim 1, wherein said plant is chosen from the genus *Geissois* or the genus *Alyssum* and the metal is Ni.

22. The method according to claim 1, wherein said plant is *Bacopa monnieri* and the metal is Cu.

* * * * *